United States Patent [19]

Amemiya et al.

[11] Patent Number: 4,496,745

[45] Date of Patent: Jan. 29, 1985

[54] EPOXYCARBACYCLIN DERIVATIVES, THEIR PREPARATION AND USE

[75] Inventors: Shigeo Amemiya; Koichi Kojima, both of Hiromachi, Japan

[73] Assignee: Sankyo Company, Limited, Tokyo, Japan

[21] Appl. No.: 545,097

[22] Filed: Oct. 25, 1983

[30] Foreign Application Priority Data

Oct. 26, 1982 [JP]  Japan ................ 57/187760

[51] Int. Cl.³ ............... C07D 303/40; C07D 407/14; C07D 407/08; C07F 7/18
[52] U.S. Cl. ................... 549/215; 549/332; 549/28; 560/119
[58] Field of Search ............. 549/332, 215, 28; 542/401

[56] References Cited

U.S. PATENT DOCUMENTS 4,322,435  3/1982  Kojima et al. .............. 424/305

*Primary Examiner*—Norma S. Milestone
*Attorney, Agent, or Firm*—Frishauf, Holtz, Goodman & Woodward

[57] ABSTRACT

Compounds of formula (I):

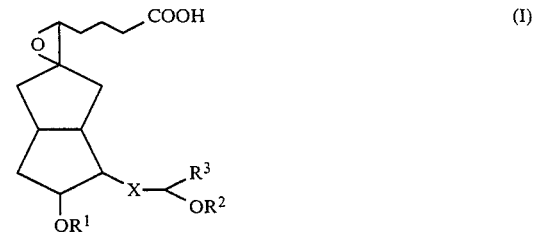

(in which:
$R^1$ and $R^2$ are the same or different and each represents hydrogen or a hydroxy-protecting group:
$R^3$ represents an alkyl group having from 1 to 12 carbon atoms which is optionally substituted, an alkenyl group having from 2 to 12 carbon atoms, an alkynyl group having from 2 to 6 carbon atoms or a cycloalkyl group which is optionally substituted; and
X represents an ethylene group, a trans-vinylene group or an ethynylene group) and salts and esters thereof are useful intermediates in the conversion of 5Z-carbacyclin derivatives to their 5E-isomers and in the preparation of certain other carbacyclin compounds.

10 Claims, No Drawings

EPOXYCARBACYCLIN DERIVATIVES, THEIR PREPARATION AND USE

BACKGROUND OF THE INVENTION

The present invention relates to a series of new epoxycarbacyclin derivatives, and provides a process for preparing these derivatives from Z-isomers of corresponding carbacyclin compounds and a process for converting these derivatives to the E-isomers of the corresponding carbocyclin compounds. Overall, the two processes of the invention enable the Z-isomer of a carbacyclin compound to be converted to its corresponding E-isomer in good yield.

Carbacyclin compounds are chemically stable and have been developed for various therapeutic uses, including the treatment of thrombosis. The compounds are produced by chemical synthesis and are normally obtained as mixtures of the E- and Z-isomers with respect to the exo double bond of the compound. For example, U.S. Pat. No. 4,322,435 discloses a series of carbacyclin derivatives, many of which have a double bond at the 5-position; during the synthesis of these compounds, the product is usually obtained as a mixture of the 5E- and 5Z-isomers. However, in general, the 5E-isomer is much more active and useful than its corresponding 5Z-isomer, which may have so little activity as to be of no practical use. Since, in the chemical synthesis of carbacyclin derivatives, a substantial proportion of the starting material is converted into the undesired 5Z-isomer (which substantially reduces the yield of 5E-isomer and hence increases the overall cost of the process), it is desirable to convert the unwanted 5Z-isomer to the valuable 5E-isomer.

BRIEF DESCRIPTION OF INVENTION

We have now discovered a process which enables the 5Z-isomer of certain carbacyclin derivatives to be converted to the corresponding 5E-isomer proceding via certain novel epoxycarbacyclin derivatives.

Accordingly, the present invention provides epoxycarbacyclin derivatives of formula (I):

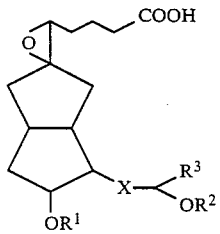
(I)

(in which:
R$^1$ and R$^2$ are the same or different and each represents hydrogen or a hydroxy-protecting group;
R$^3$ represents an alkyl group having from 1 to 12 carbon atoms which is optionally substituted, an alkenyl group having from 2 to 12 carbon atoms, an alkynyl group having from 2 to 6 carbon atoms or a cycloalkyl group which is optionally substituted; and
X represents an ethylene group, a trans-vinylene group or an ethynylene group)
and salts and esters thereof.

The invention also provides a process for preparing compounds of formula (I), as defined above, and their salts and esters, which comprises reacting a 5Z-carbacyclin derivative of formula (II):

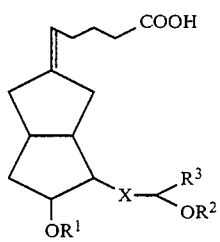
(II)

(in which R$^1$, R$^2$, R$^3$ and X are as defined above) with iodine and with an alkali metal iodide in the presence of a base to give a lactone of formula (III):

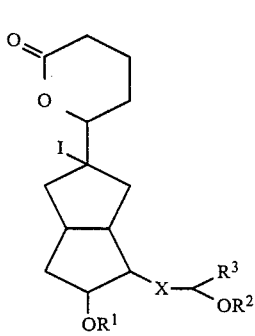
(III)

(in which R$^1$, R$^2$, R$^3$ and X are as defined above) and reacting said lactone of formula (III) with water or an alcohol, to give said compound of formula (I), and, if necessary, salifying or esterifying said compound of formula (I).

The invention further provides a process for preparing a 5E-carbacyclin derivative of formula (V):

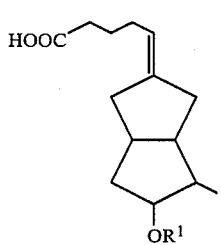
(V)

(in which R$^1$, R$^2$, R$^3$ and X are as defined above) and salts and esters thereof, which comprises reacting an epoxycarbacyclin derivative of formula (I), defined above, or a salt or ester thereof with a phosphorus compound of formula (VI):

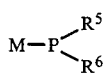
(VI)

(in which R$^5$ and R$^6$ are the same or different and each represents an alkyl group having from 1 to 6 carbon atoms, an aralkyl group or an aryl group and M represents an alkali metal atom) and then treating the product with a compound of formula (VII):

(VII)

(in which R[7] represents an alkyl group having from 1 to 4 carbon atoms, or an aralkyl group and Q represents a halogen atom, an alkanesulphonyloxy group or an arylsulphonyloxy group), to give said compound of formula (V) or a salt or ester thereof.

In a preferred embodiment, the invention provides a process for converting a 5Z-carbacyclin derivative of formula (II) to its corresponding 5E-carbacyclin compound of formula (V) by preparing said epoxycarbacyclin derivative of formula (I) or a salt or ester thereof from said 5Z-carbacyclin derivative of formula (II), by the first-mentioned process of the invention and then converting said epoxycarbacyclin derivative of formula (I) or salt or ester thereof to said 5E-carbacyclin derivative of formula (V) or a salt or ester thereof by the second-mentioned process of the invention.

DETAILED DESCRIPTION OF INVENTION

The compounds of the invention can exist in the form of various geometric isomers and other stereoisomers, particularly with respect to the double ring system. Preferred isomers of the compounds of formula (I) are those of formula (Ia):

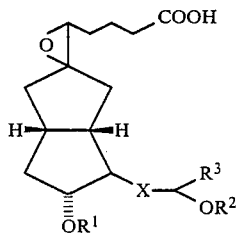
(Ia)

(in which $R^1$, $R^2$, $R^3$ and X are as defined above) and the salts and esters preferably have a corresponding configuration. Accordingly, compounds of formulae (II), (III) and (V) preferably have an equivalent configuration, e.g. compounds of formula (Va):

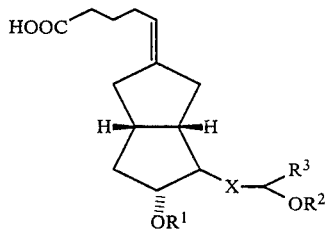
(Va)

(in which $R^1$, $R^2$, $R^3$ and X are as defined above), the salts and esters preferably having a corresponding configuration.

In the compounds of formulae (I), (II), (III) and (V), $R^1$ and $R^2$ may be the same or different and each represents a hydrogen atom or a hydroxy-protecting group. Although $R^1$ and $R^2$ may be different, we prefer that either both should be hydrogen atoms or both should be hydroxy-protecting groups. Where both $R^1$ and $R^2$ represent hydroxy-protecting groups, these likewise may be the same or different, but it is generally more convenient if the two hydroxy-protecting groups represented by $R^1$ and $R^2$ are the same. In general, prior to any therapeutic use of the compounds, any hydroxy-protecting groups represented by $R^1$ and $R^2$ will be removed from the compound. Accordingly, since these groups are removed, they have no effect on the therapeutic activity of any compounds and they may, accordingly, be chosen solely for their convenience and/or effectiveness as hydroxy-protecting groups. Accordingly, any hydroxy-protecting groups known in the art for use with compounds of this type may equally be employed in the present invention, without any restriction. One preferred class of hydroxy-protecting groups comprises substituted $C_1$–$C_4$ alkyl groups having a $C_1$–$C_4$ alkoxy, $C_1$–$C_4$ alkylthio, trihalomethyl or aralkyloxy substituent at the α-position; specific examples include the methoxymethyl, ethoxymethyl, propoxymethyl, isopropoxymethyl, butoxymethyl, methylthiomethyl, ethylthiomethyl, propylthiomethyl, isopropylthiomethyl, butylthiomethyl, benzyloxymethyl, p-nitrobenzyloxymethyl, p-bromobenzyloxymethyl, 2,2,2-trichloroethyl, 2,2,2-tribromoethyl, 1-methoxyethyl, 1-ethoxyethyl, 1-methoxy-1-methylethyl or 1-ethyl-1-methoxyethyl groups. Where the substituent on the alkyl group is an alkoxy, alkylthio or aralkyloxy group, this substituent may itself be substituted, the substituents being, for example, those suggested as substituents for the alkyl group or they may be alkyl groups. An example of such a substituted group is the 2-methoxyethoxymethyl group. Other preferred substituents on alkyl groups represented by $R^1$ or $R^2$ include aryl groups, i.e. the hydroxy-protecting group represented by $R^1$ or $R^2$ is an aralkyl group; examples of such aralkyl groups include the benzyl, p-nitrobenzyl, p-bromobenzyl, 1-methyl-1-phenylethyl, 1-ethyl-1-phenylethyl, diphenylmethyl and trityl (triphenylmethyl) groups.

Other hydroxy-protecting groups which may be represented by $R^1$ and/or $R^2$ include heterocyclic groups, such as the 4-methoxytetrahydrothiopyran-4-yl group and groups of formula

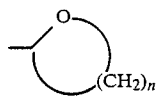

(in which n is an integer of from 3 to 5).

Other preferred hydroxy-protecting groups which may be represented by $R^1$ and/or $R^2$ include trialkylsilyl, dialkylphenylsilyl and diphenylalkylsilyl groups, in which the or each alkyl group has from 1 to 4 carbon atoms. Examples of such groups include the trimethylsilyl, triethylsilyl, dimethylisopropylsilyl, t-butyl-dimethylsilyl, dimethylphenylsilyl and diphenyl-t-butylsilyl groups.

Further preferred hydroxy-protecting groups which may be represented by $R^1$ and/or $R^2$ include acyl groups, especially carboxylic acyl groups and most preferably alkanoyl or arylcarbonyl groups, such as the acetyl, propionyl, butyryl, benzoyl and p-methylbenzoyl groups.

However, it should be emphasized that the above hydroxy-protecting groups are given for exemplification only and that, because of the non-criticality of the groups represented by $R^1$ and $R^2$, any hydroxy-protecting group may be employed in this position, provided that it may be introduced and removed without substantially affecting the remainder of the molecule.

Preferred hydroxy-protecting groups represented by $R^1$ and $R^2$ include: substituted $C_1$–$C_4$ alkyl groups having one or more $C_1$–$C_4$ alkoxy, $C_1$–$C_4$ alkylthio, trihalomethyl or aralkyloxy, substituents at the α-position; the 2-methoxyethoxymethyl group; the tetrahydrofuran- 2-yl group; the tetrahydropyran-2-yl group; the 4-methoxytetrahydrothiopyran-4-yl group; a trialkylsilyl or dialkylphenylsilyl group in which each alkyl group has from 1 to 4 carbon atoms; the acetyl group; the propionyl group; or the benzoyl group. Particularly preferred hydroxy-protecting groups which may be represented by $R^1$ and/or $R^2$ are the methoxymethyl, tetrahydropyran-2-yl, t-butyldimethylsilyl, acetyl and benzoyl groups.

$R^3$ represents an optionally substituted $C_1$-$C_{12}$ alkyl group, a $C_2$-$C_{12}$ alkenyl group, a $C_2$-$C_6$ alkynyl group or an optionally substituted cycloalkyl group.

Where $R^3$ represents an optionally substituted alkyl group, the alkyl group, which may be a straight or branched chain group, may be, for example, a methyl, ethyl, propyl, isopropyl, butyl, isobutyl, pentyl, isopentyl, 1-methylpentyl, 2-methylpentyl, hexyl, heptyl, 1,1-dimethylpentyl, 1-methylhexyl, 2-methylhexyl, 2-ethylpentyl, octyl, 2-methyloctyl, nonyl, 2-methylnonyl, 2-ethyloctyl, decyl, 2-methyldecyl or 2-ethyldecyl group.

A wide range of substituents is possible on the alkyl group represented by $R^3$, for example halogen atoms, alkoxy groups, optionally substituted cycloalkyl groups, optionally substituted aryl groups and groups of formula —Y—A (in which Y represents an oxygen or sulphur atom or an —NH group and A represents an optionally substituted aryl group). Where $R^3$ represents an unsubstituted alkyl group or a substituted alkyl group having a halogen or alkoxy substituent, the alkyl group is preferably a $C_4$-$C_{10}$ alkyl group, for example a butyl, isobutyl, pentyl, isopentyl, 1-methylpentyl, 2-methylpentyl, hexyl, heptyl, 1,1-dimethylpentyl, 1-methylhexyl, 2-methylhexyl, 2-ethylpentyl, octyl, 2-methyloctyl or 2-ethyloctyl group, more preferably a pentyl, 1-methylpentyl, hexyl, 1,1-dimethylpentyl, 1-methylhexyl or 2-methylhexyl group. Where $R^3$ represents a substituted alkyl group having an optionally substituted cycloalkyl, optionally substituted aryl or —Y—A substituent, the alkyl group preferably has from 1 to 3 carbon atoms, i.e. a methyl, ethyl, propyl or isopropyl group, more preferably a methyl or ethyl group.

Where the substituent on the alkyl group represented by $R^3$ is a halogen atom, this is preferably a fluorine, chlorine or bromine atom. Where the substituent on the alkyl group represented by $R^3$ is an alkoxy group, it is preferably a $C_1$-$C_4$ alkoxy group, which may be a straight or branched chain group, for example a methoxy, ethoxy, propoxy, isopropoxy or butoxy group.

Where $R^3$ represents a cycloalkyl group or a substituted alkyl group having an optionally substituted cycloalkyl substituent, the cycloalkyl group preferably has from 3 to 7 ring carbon atoms and examples include the cyclopropyl, cyclobutyl, cyclopentyl, cyclohexyl and cycloheptyl groups. Examples of substituents on these cycloalkyl groups include: halogen atoms, such as fluorine, chlorine or bromine atoms; alkyl groups having from 1 to 4 carbon atoms, such as methyl, ethyl, propyl, isopropyl and butyl groups; and the trifluoromethyl group; preferred substituents are the methyl and ethyl groups. Where the cycloalkyl group is a substituent on an alkyl group represented by $R^3$, it is preferably a cyclopentyl or cyclohexyl group, which may be unsubstituted or may have one or more substituents as noted above. Where the cycloalkyl group itself is represented by $R^3$, it is preferably a cyclohexyl, cyclopentyl or 1-butylcyclopropyl group.

Where the substituent on the alkyl group represented by $R^3$ is an optionally substituted aryl group or a group of formula —Y—A. A representing an optionally substituted aryl group, the aryl group is preferably a phenyl or naphthyl group, more preferably a phenyl group. This aryl group may be substituted or unsubstituted; where it is substituted, examples of suitable substituents are the same as those given as substituents for cycloalkyl groups in the preceding paragraph. Where the substituent on the alkyl group represented by $R^3$ is a group of formula —Y—A. Y may represent an oxygen atom, a sulphur atom or an —NH group, preferably an oxygen atom or a sulphur atom.

Particularly preferred substituents on the alkyl group represented by $R^3$ include the fluorine atom and methoxy, ethoxy, cyclopentyl, 3-methylcyclopentyl, 3-ethylcyclopentyl, cyclohexyl, 3-methylcyclohexyl, 3-ethylcyclohexyl, phenyl, m-chlorophenyl, phenoxy, phenylthio and p-trifluoromethylphenoxy groups.

Where $R^3$ represents an alkenyl group, it is a group having from 2 to 12 carbon atoms and may be a straight or branched chain group. Examples of such groups include the vinyl, allyl, 2-butenyl, 2-pentenyl, 3-pentenyl, 4-pentenyl, 2-methyl-3-pentenyl, 4-methyl-3-pentenyl, 1-methyl-4-pentenyl, 4-hexenyl, 5-hexenyl, 1,4-dimethyl-3-pentenyl, 5-heptenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl and 2,6-diethyl-5-octenyl groups. We prefer alkenyl groups having from 4 to 12 carbon atoms, for example the 2-butenyl, 2-pentenyl, 3-pentenyl, 4-pentenyl, 2-methyl-3-pentenyl, 4-methyl-3-pentenyl, 1-methyl-4-pentenyl, 4-hexenyl, 5-hexenyl, 1,4-dimethyl-3-pentenyl, 5-heptenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl and 2,6-diethyl-5-octenyl groups, more preferably the 2-pentenyl, 4-pentenyl, 4-hexenyl, 5-hexenyl, 6-methyl-5-heptenyl and 2,6-dimethyl-5-heptenyl groups.

Where $R^3$ represents an alkynyl group having from 2 to 6 carbon atoms, it may be a straight or branched chain group; examples include the ethynyl, propargyl, 2-butynyl, 2-pentynyl, 3-pentynyl, 1-methyl-2-butynyl, 2-hexynyl, 1-methyl-2-pentynyl and 1-methyl-3-pentynyl groups, of which we prefer the alkynyl groups having from 4 to 6 carbon atoms such as the 2-butynyl, 2-pentynyl, 3-pentynyl, 1-methyl-2-pentynyl and 1-methyl-3-pentynyl groups, most preferably the 1-methyl-3-pentynyl group.

X, which may represent an ethylene, trans-vinylene or ethynylene group, is preferably an ethylene or trans-vinylene group.

Where the compound of the invention is an ester, it is preferably a $C_1$-$C_4$ alkyl ester or an aralkyl ester. Particularly preferred compounds of formula (I) are, accordingly, those of formula (Ib), whilst particularly preferred compounds of formula (V) are those of formula (Vb):

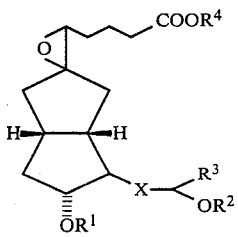

(Ib)

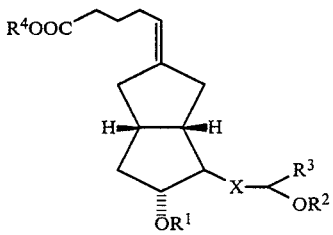

(Vb)

(in which R¹, R², R³ and X are as defined above and R⁴ represents a hydrogen atom, a $C_1$–$C_4$ alkyl group or an aralkyl group).

Examples of $C_1$–$C_4$ alkyl groups, which may be represented by R⁴ in the compounds of formulae (Ib) and (Vb) and which may be the ester moiety of esters of compounds of formulae (I) and (V) include straight or branched chain groups, preferably a methyl, ethyl, propyl, isopropyl or butyl group, more preferably a methyl or ethyl group. Examples of aralkyl groups, which may be represented by R⁴ or may be the aforesaid ester moiety include the benzyl, p-bromobenzyl and p-nitrobenzyl groups, more preferably the benzyl group.

Compounds of formula (I) form salts and these salts, preferably with a pharmaceutically acceptable cation [although, since the compounds of formula (I) are intermediates, this is not essential], also form part of the present invention. Examples of such salts include salts with alkali metals, such as lithium, sodium or potassium, preferably sodium or potassium.

Particularly preferred classes of compound of formula (I), (Ia) and (Ib) are as follows:

(A) Compounds in which:
R¹ and R² are the same or different and each represents a hydrogen atom or a hydroxy-protecting group;
R³ represents a $C_4$–$C_{10}$ alkyl group which is unsubstituted or which has one or more fluorine, methoxy or ethoxy substituents; a $C_1$–$C_3$ alkyl group having one or more cyclopentyl, 3-methylcyclopentyl, 3-ethylcyclopentyl, cyclohexyl, 3-methylcyclohexyl, 3-ethylcyclohexyl, phenyl, p-trifluoromethylphenoxy, phenoxy, phenylthio or p-tolyloxy substituents; a $C_4$–$C_{12}$ alkenyl group; a $C_4$–$C_6$ alkynyl group; a cyclopentyl group; a 3-methylcyclopentyl group; a 3-ethylcyclopentyl group; a cyclohexyl group; a 3-methylcyclohexyl group; or a 3-ethylcyclohexyl group; and
X represents an ethylene, trans-vinylene or ethynylene group;
and salts and aralkyl and $C_1$–$C_4$ alkyl esters thereof.

(B) Compounds in which:
R³ and X are as defined for class (A) and in which R¹ and R² are the same or different and each represents: a hydrogen atom; a $C_1$–$C_4$ alkyl group having at its α-position a $C_1$–$C_4$ alkoxy, $C_1$–$C_4$ alkylthio, aralkyloxy or trihalomethyl substituent; a 2-methoxyethoxymethyl group; a tetrahydrofuran-2-yl group; a tetrahydropyran-2-yl group; a 4-methoxytetrahydrothiopyran-4-yl group; a trialkylsilyl or dialkylphenylsilyl group, in which each alkyl group has from 1 to 4 carbon atoms; an acetyl group; a propionyl group; or a benzoyl group;
and salts and aralkyl and $C_1$–$C_4$ alkyl esters thereof.

(C) Compounds in which:
R¹ and R² are the same or different and each represents a hydrogen atom or a methoxymethyl, tetrahydropyran-2-yl, t-butyl-dimethylsilyl, acetyl or benzoyl group;
R³ represents a pentyl, 1-methylpentyl, hexyl, 1-methylhexyl, 1,1-dimethylpentyl, 2-methylhexyl, 2-ethoxy-1,1-dimethylethyl, 5-methoxypentyl, 5-methoxy-1-methylpentyl, 1-fluoropentyl, cyclopentylmethyl, 3-methylcyclopentylmethyl, 2-cyclopentylethyl, 2-cyclopentyl-1-methylethyl, cyclohexylmethyl, 3-ethylcyclohexylmethyl, 2-cyclohexylethyl, benzyl, phenethyl, p-methylbenzyl, phenoxymethyl, m-chlorophenoxymethyl, phenylthiomethyl, 2-pentenyl, 4-pentenyl, 4-hexenyl, 5-hexenyl, 6-methyl-5-heptenyl, 2,6-dimethyl-5-heptenyl, 3-pentynyl, 1-methyl-2-pentynyl, 1-methyl-3-pentynyl, cyclopentyl, 3-ethylcyclopentyl, cyclohexyl, 3-methylcyclohexyl or 1-butylcyclopropyl group; and
X represents an ethylene or trans-vinylene group;
and salts and methyl or ethyl esters thereof.

(D) Compounds in which:
R¹ and R² are the same or different and each represents a hydrogen atom, a tetrahydropyran-2-yl group, a t-butyl-dimethylsilyl group or an acetyl group;
R³ represents a pentyl, 1-methylhexyl, 1,1-dimethylpentyl, 5-methoxypentyl, phenoxymethyl, 2-pentenyl, 4-pentenyl, 4-hexenyl, 5-hexenyl, 6-methyl-5-heptenyl, 2,6-dimethyl-5-heptenyl, 1-methyl-3-pentynyl or cyclopentyl group; and
X represents a trans-vinylene group;
and salts and methyl esters thereof.

As is conventional, the compounds of the invention are named as derivatives of prostanoic acid. Thus, the nomenclature is based upon compounds in which R³ represents a $C_5$ group and the numbering system employed is as shown on the following skeletal structure:

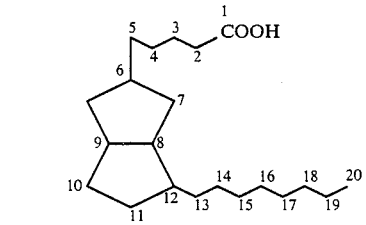

Compounds in which R³ represents a group having fewer than 5 carbon atoms are designated by the prefix "nor", "dinor" etc. which denotes the elimination of 1 or 2 etc. methylene groups from the carbon chain in the above skeletal structure, whilst compounds in which R³ represents a group having more than 5 carbon atoms are designated by the prefix "homo", "dihomo" etc, which denotes the insertion of 1 or 2 etc methylene groups into the carbon chain in the above skeletal structure.

Examples of preferred compounds of formula (I) are given in the following list:

1. 5,6-Epoxy-6,9α-methylene-11α,15α-bis(2-tetrahydropyranyloxy)-20-norprost-13(E)-enoic acid
2. 5,6-Epoxy-6,9α-methylene-11α,15α-bis(2-tetrahydropyranyloxy)prostanoic acid
3. 5,6-Epoxy-6,9α-methylene-11α,15α-bis(2-tetrahydropyranyloxy)prost-13(E)-enoic acid
4. 5,6-Epoxy-6,9α-methylene-11α,15α-bis(2-tetrahydrofuranyloxy)prost-13-ynoic acid
5. 5,6-Epoxy-6,9α-methylene-11α,15α-bis(2-tetrahydropyranyloxy)-17-methyl-20-norprostanoic acid
6. 5,6-Epoxy-6,9α-methylene-11α,15α-bis(2-tetrahydropyranyloxy)-20-methylprost-13(E)-enoic acid
7. 5,6-Epoxy-6,9α-methylene-11α,15α-bis(2-tetrahydropyranyloxy)-17-methylprostanoic acid
8. 5,6-Epoxy-6,9α-methylene-11α,15α-diacetoxy-18-methylprostanoic acid
9. 5,6-Epoxy-6,9α-methylene-11α,15α-bis(2-tetrahydropyranyloxy)-20-ethylprost-13(E)-enoic acid
10. 5,6-Epoxy-6,9α-methylene-11α,15α-diacetoxy-17,20-dimethylprostanoic acid
11. 5,6-Epoxy-6,9α-methylene-11α,15α-bis(2-tetrahydropyranyloxy)-17,20-dimethylprost-13(E)-enoic acid
12. 5,6-Epoxy-6,9α-methylene-11α,15α-bis(t-butyldimethylsilyloxy)-16,16-dimethylprostanoic acid
13. 5,6-Epoxy-6,9α-methylene-11α,15α-bis(2-tetrahydropyranyloxy)-16,16-dimethylprost-13(E)-enoic acid
14. 5,6-Epoxy-6,9α-methylene-11α,15α-dibenzoyloxy-16-fluoroprostanoic acid
15. 5,6-Epoxy-6,9α-methylene-11α,15α-bis-(2-tetrahydropyranyloxy)-20-methoxyprostanoic acid
16. 5,6-Epoxy-6,9α-methylene-11α,15α-bis(2-tetrahydropyranyloxy)-20-methoxyprost-13(E)-enoic acid
17. 5,6-Epoxy-6,9α-methylene-11α,15α-bis(2-tetrahydropyranyloxy)16-methyl-19-methoxy-20-norprost-13(E)-enoic acid
18. 5,6-Epoxy-6,9α-methylene-11α,15α-bis(2-tetrahydrofuranyloxy)-16-methyl-19-methoxy-20-norprost-13-ynoic acid
19. 5,6-Epoxy-6,9α-methylene-11α,15α-bis(methoxymethoxy)-16,16-dimethyl-17-ethoxy-18,19,20-trinorprostanoic acid
20. 5,6-Epoxy-6,9α-methylene-11α,15α-diacetoxy-16,16-dimethyl-17-ethoxy-18,19,20-trinorprost-13(E)-enoic acid
21. 5,6-Epoxy-6,9α-methylene-11α,15α-bis(2-tetrahydropyranyloxy)prost-13(E),19-dienoic acid
22. 5,6-Epoxy-6,9α-methylene-11α,15α-diacetoxyprost-18-enoic acid
23. 5,6-Epoxy-6,9α-methylene-11α,15α-bis(2-tetrahydropyranyloxy)prost-13(E),18-dienoic acid
24. 5,6-Epoxy-6,9α-methylene-11α,15α-bis(2-tetrahydropyranyloxy)prost-17-enoic acid
25. 5,6-Epoxy-6,9α-methylene-11α,15α-bis(2-tetrahydropyranyloxy)prost-13(E),17-dienoic acid
26. 5,6-Epoxy-6,9α-methylene-11α,15α-bis(t-butyldimethylsilyloxy)prost-13-yn-17-enoic acid
27. 5,6-Epoxy-6,9α-methylene-11α,15α-bis(2-tetrahydropyranyloxy)-20-methyleneprostanoic acid
28. 5,6-Epoxy-6,9α-methylene-11α,15α-bis(2-tetrahydropyranyloxy)-20-methylprost-13(E),19-dienoic acid
29. 5,6-Epoxy-6,9α-methylene-11α,15α-bis(t-butyldimethylsilyloxy)-16,20-dimethylprost-13(E),19-dienoic acid
30. 5,6-Epoxy-6,9α-methylene-11α,15α-bis(2-tetrahydropyranyloxy)-16,19-dimethylprost-18-enoic acid
31. 5,6-Epoxy-6,9α-methylene-11α,15α-bis(2-tetrahydropyranyloxy)-20-isopropylideneprostanoic acid
32. 5,6-Epoxy-6,9α-methylene-11α,15α-diacetoxy-20-isopropylideneprost-13(E)-enoic acid
33. 5,6-Epoxy-6,9α-methylene-11α,15α-bis(t-butyldimethylsilyloxy)-20-isopropylideneprost-13-ynoic acid
34. 5,6-Epoxy-6,9α-methylene-11α,15α-bis(2-tetrahydropyranyloxy)-16,20,20-trimethylprost-19-enoic acid
35. 5,6-Epoxy-6,9α-methylene-11α,15α-bis(methoxymethoxy)-16,20,20-trimethylprost-13(E),19-dienoic acid
36. 5,6-Epoxy-6,9α-methylene-11α,15α-bis(2-tetrahydropyranyloxy)-20-(2-methyl-1-propenyl)prostanoic acid
37. 5,6-Epoxy-6,9α-methylene-11α,15α-bis(2-tetrahydropyranyloxy)-20-(2-methyl-1-propenyl)prost-13(E)-enoic acid
38. 5,6-Epoxy-6,9α-methylene-11α,15α-bis(2-tetrahydropyranyloxy)-16-methyl-20-isopropylideneprost-13(E)-enoic acid
39. 5,6-Epoxy-6,9α-methylene-11α,15α-bis(2-tetrahydropyranyloxy)-17-methyl-20-isopropylideneprostanoic acid
40. 5,6-Epoxy-6,9α-methylene-11α,15α-bis(2-tetrahydropyranyloxy)-17-methyl-20-isopropylideneprost-13(E)-enoic acid
41. 5,6-Epoxy-6,9α-methylene-11α,15α-diacetoxy-17β-methyl-20-isopropylideneprost-13(E)-enoic acid
42. 5,6-Epoxy-6,9α-methylene-11α,15α-bis(t-butyldimethylsilyloxy)-17-methyl-20-isopropylideneprost-13-ynoic acid
43. 5,6-Epoxy-6,9α-methylene-11α,15α-bis(2-tetrahydropyranyloxy)-20-(1-ethylpropylidene)prost-13(E)-enoic acid
44. 5,6-Epoxy-6,9α-methylene-11α,15α-bis(2-tetrahydropyranyloxy)-17-methyl-20-(1-ethylpropylidene)prost-13(E)-enoic acid
45. 5,6-Epoxy-6,9α-methylene-11α,15α-bis(t-butyldimethylsilyloxy)-16-methylprost-18-ynoic acid
46. 5,6-Epoxy-6,9α-methylene-11α,15α-bis(2-tetrahydropyranyloxy)-16-methyl-20-norprost-13(E)-en-17-ynoic acid
47. 5,6-Epoxy-6,9α-methylene-11α,15α-bis(2-tetrahydropyranyloxy)-16-methylprost-17-ynoic acid
48. 5,6-Epoxy-6,9α-methylene-11α,15α-bis(2-tetrahydropyranyloxy)-16-methylprost-13(E)-en-17-ynoic acid
49. 5,6-Epoxy-6,9α-methylene-11α,15α-dibenzoyloxy-16-methylprost-13(E)-en-17-ynoic acid
50. 5,6-Epoxy-6,9α-methylene-11α,15α-bis(2-tetrahydropyranyloxy)-15-cyclopentyl-16,17,18,19,20-pentanorprostanoic acid
51. 5,6-Epoxy-6,9α-methylene-11α,15α-dibenzoyloxy-15-cyclopentyl-16,17,18,19,20-pentanorprostanoic acid
52. 5,6-Epoxy-6,9α-methylene-11α,15α-bis(2-tetrahydropyranyloxy)-15-cyclopentyl-16,17,18,19,20-pentanorprost-13(E)-enoic acid
53. 5,6-Epoxy-6,9α-methylene-11α,15α-bis(t-butyldimethylsilyloxy)-15-cyclopentyl-16,17,18,19,20-pentanorprost-13(E)-enoic acid
54. 5,6-Epoxy-6,9α-methylene-11α,15α-bis(benzyloxymethoxy)-15-cyclopentyl-16,17,18,19,20-pentanorprost-13-ynoic acid 55. 5,6-Epoxy-6,9α-methylene-11α,15α-dipropionyloxy-15-(3-ethylcyclopentyl)-16,17,18,19,20-pentanorprost-13(E)-enoic acid
56. 5,6-Epoxy-6,9α-methylene-11α,15α-bis(2-tetrahydropyranyloxy)-15-cyclohexyl-16,17,18,19,20-pentanorprostanoic acid
57. 5,6-Epoxy-6,9α-methylene-11α,15α-bis(2-tetrahydropyranyloxy)-15-cyclohexyl-16,17,18,19,20-pentanorprost-13(E)-enoic acid
58. 5,6-Epoxy-6,9α-methylene-11α,15α-bis(2-tetrahydropyranyloxy)-16,16-ethyleneprostanoic acid
59. 5,6-Epoxy-6,9α-methylene-11α,15α-bis(2-tetrahydrofuranyloxy)-16,16-ethyleneprost-13(E)-enoic acid
60. 5,6-Epoxy-6,9α-methylene-11α,15α-bis(2-tetrahydropyranyloxy)-16,16-ethyleneprost-13-ynoic acid
61. 5,6-Epoxy-6,9α-methylene-11α,15α-bis(2-tetrahydropyranyloxy)-16-cyclopentyl-17,18,19,20-tetranorprostanoic acid
62. 5,6-Epoxy-6,9α-methylene-11α,15α-bis(t-butyldimethylsilyloxy)-16-cyclopentyl-17,18,19,20-tetranorprost-13(E)-enoic acid
63. 5,6-Epoxy-6,9α-methylene-11α,15α-diacetoxy-16-(3-methylcyclopentyl)-17,18,19,20-tetranorprostanoic acid
64. 5,6-Epoxy-6,9α-methylene-11α,15α-bis(2-tetrahydropyranyloxy)-16-(3-ethylcyclopentyl)-17,18,19,20-tetranorprost-13-ynoic acid
65. 5,6-Epoxy-6,9α-methylene-11α,15α-bis(t-butyldimethylsilyloxy)-16-cyclohexyl-17,18,19,20-tetranorprostanoic acid
66. 5,6-Epoxy-6,9α-methylene-11α,15α-bis(2-tetrahydropyranyloxy)-16-cyclohexyl-17,18,19,20-tetranorprost-13(E)-enoic acid
67. 5,6-Epoxy-6,9α-methylene-11α,15α-diacetoxy-17-cyclopentyl-18,19,20-trinorprostanoic acid
68. 5,6-Epoxy-6,9α-methylene-11α,15α-diacetoxy-17-(3-methylcyclopentyl)-18,19,20-trinorprost-13(E)-enoic acid
69. 5,6-Epoxy-6,9α-methylene-11α,15α-bis(2-tetrahydropyranyloxy)-17-cyclohexyl-18,19,20-trinorprost-13(E)-enoic acid
70. 5,6-Epoxy-6,9α-methylene-11α,15α-bis(2-tetrahydropyranyloxy)-16-methyl-17-cyclopentyl-18,19,20-trinorprostanoic acid
71. 5,6-Epoxy-6,9α-methylene-11α,15α-bis(t-butyldimethylsilyloxy)-16-methyl-17-cyclohexyl-18,19,20-trinorprost-13(E)-enoic acid
72. 5,6-Epoxy-6,9α-methylene-11α,15α-bis(2-tetrahydropyranyloxy)-16,16-dimethyl-17-cyclopentyl-18,19,20-trinorprostanoic acid
73. 5,6-Epoxy-6,9α-methylene-11α,15α-bis(2-tetrahydrofuranyloxy)-16,16-dimethyl-18-cyclohexyl-19,20-dinorprost-13(E)-enoic acid
74. 5,6-Epoxy-6,9α-methylene-11α,15α-bis(t-butyldimethylsilyloxy)-16-phenyl-17,18,19,20-tetranorprostanoic acid
75. 5,6-Epoxy-6,9α-methylene-11α,15α-diacetoxy-16-phenyl-17,18,19,20-tetranorprost-13(E)-enoic acid
76. 5,6-Epoxy-6,9α-methylene-11α,15α-bis(2-tetrahydropyranyloxy)-16-(m-chlorophenyl)-17,18,19,20-tetranorprostanoic acid
77. 5,6-Epoxy-6,9α-methylene-11α,15α-bis(2-tetrahydrofuranyloxy)-17-phenyl-18,19,20-trinorprost-13(E)-enoic acid
78. 5,6-Epoxy-6,9α-methylene-11α,15α-bis(2-tetrahydropyranyloxy)-17-(m-bromophenyl)-18,19,20-trinorprostanoic acid
79. 5,6-Epoxy-6,9α-methylene-11α,15α-dibenzoyloxy-17-(m-trifluoromethylphenyl)-18,19,20-trinorprost-13(E)-enoic acid
80. 5,6-Epoxy-6,9α-methylene-11α,15α-bis(2-tetrahydropyranyloxy)-16-phenoxy-17,18,19,20-tetranorprostanoic acid
81. 5,6-Epoxy-6,9α-methylene-11α,15α-bis(2-tetrahydropyranyloxy)-16-phenoxy-17,18,19,20-tetranorprost-13(E)-enoic acid
82. 5,6-Epoxy-6,9α-methylene-11α,15α-bis(t-butyldimethylsilyloxy)-16-p-tolyloxy-17,18,19,20-tetranorprostanoic acid
83. 5,6-Epoxy-6,9α-methylene-11α,15α-diacetoxy-16-(m-trifluoromethylphenoxy)-17,18,19,20-tetranorprost-13(E)-enoic acid
84. 5,6-Epoxy-6,9α-methylene-11α,15α-bis(2-tetrahydropyranyloxy)-16-(m-chlorophenoxy)-17,18,19,20-tetranorprost-13(E)-enoic acid
85. 5,6-Epoxy-6,9α-methylene-11α,15α-bis(2-tetrahydrofuranyloxy)-16-(o-fluorophenoxy)-17,18,19,20-tetranorprostanoic acid
86. 5,6-Epoxy-6,9α-methylene-11α,15α-bis(2-tetrahydropyranyloxy)-16-phenylthio-17,18,19,20-tetranorprostanoic acid
87. 5,6-Epoxy-6,9α-methylene-11α,15α-bis(2-tetrahydropyranyloxy)-16-phenylthio-17,18,19,20-tetranorprost-13(E)-enoic acid
88. 5,6-Epoxy-6,9α-methylene-11α,15α-diacetoxy-16-m-tolylthio-17,18,19,20-tetranorprostanoic acid
89. 5,6-Epoxy-6,9α-methylene-11α,15α-diacetoxy-16-(p-bromophenylthio)-17,18,19,20-tetranorprostanoic acid
90. 5,6-Epoxy-6,9α-methylene-11α,15α-bis(2-tetrahydropyranyloxy)-16-phenylamino-17,18,19,20-tetranorprostanoic acid
91. 5,6-Epoxy-6,9α-methylene-11α,15α-bis(2-tetrahydrofuranyloxy)-16-phenylamino-17,18,19,20-tetranorprost-13(E)-enoic acid
92. 5,6-Epoxy-6,9α-methylene-11α-hydroxy-15a-(2-tetrahydropyranyloxy)prostanoic acid
93. 5,6-Epoxy-6,9α-methylene-11α-(2-tetrahydropyranyloxy)-15α-hydroxyprost-13(E)-enoic acid
94. 5,6-Epoxy-6,9α-methylene-11α,15α-dihydroxyprostanoic acid
95. 5,6-Epoxy-6,9α-methylene-11α,15α-dihydroxyprost-13(E)-enoic acid
96. 5,6-Epoxy-6,9α-methylene-11α,15α-dihydroxyprost-13-ynoic acid
97. 5,6-Epoxy-6,9α-methylene-11α-hydroxy-15α-(2-tetrahydrofuranyloxy)prostanoic acid
98. 5,6-Epoxy-6,9α-methylene-11α-(2-tetrahydrofuranyloxy)-15α-hydroxyprost-13(E)-enoic acid
99. 5,6-Epoxy-6,9α-methylene-11α-(2-tetrahydropyranyloxy)-15α-acetoxyprost-13(E)-enoic acid
100. 5,6-Epoxy-6,9α-methylene-11α-hydroxy-15α-acetoxyprost-13(E)-enoic acid
101. 5,6-Epoxy-6,9α-methylene-11α-(t-butyldimethylsilyloxy)-15α-hydroxyprostanoic acid
102. 5,6-Epoxy-6,9α-methylene-11α-(t-butyldimethylsilyloxy)-15α-acetoxyprost-13(E)-enoic acid 103. 5,6-Epoxy-6,9α-methylene-11α-(2-tetrahydropyranyloxy)-15α-(2-tetrahydrofuranyloxy)-prostanoic acid
104. 5,6-Epoxy-6,9α-methylene-11α-acetoxy-15α-hydroxyprost-13(E)-enoic acid
105. 5,6-Epoxy-6,9α-methylene-11α,15α-dihydroxy-17,20-dimethylprostanoic acid
106. 5,6-Epoxy-6,9α-methylene-11α,15α-dihydroxy-17,20-dimethylprost-13(E)-enoic acid
107. 5,6-Epoxy-6,9α-methylene-11α,15α-dihydroxy-16,16-dimethylprost-13(E)-enoic acid
108. 5,6-Epoxy-6,9α-methylene-11α,15α-dihydroxy-20-methoxyprostanoic acid
109. 5,6-Epoxy-6,9α-methylene-11α,15α-dihydroxy-16,16-dimethyl-17-ethoxy-18,19,20-trinorprost-13(E)-enoic acid
110. 5,6-Epoxy-6,9α-methylene-11α,15α-dihydroxy-prost-17-enoic acid
111. 5,6-Epoxy-6,9α-methylene-11α,15α-dihydroxy-20-isopropylideneprostanoic acid
112. 5,6-Epoxy-6,9α-methylene-11α,15α-dihydroxy-17β-methyl-20-isopropylideneprost-13(E)-enoic acid
113. 5,6-Epoxy-6,9α-methylene-11α-hydroxy-15α-(2-tetrahydropyranyloxy)-17-methyl-20-isopropylideneprostanoic acid
114. 5,6-Epoxy-6,9α-methylene-11α-(2-tetrahydropyranyloxy)-15α-hydroxy-17-methyl-20-isopropylideneprost-13(E)-enoic acid
115. 5,6-Epoxy-6,9α-methylene-11α,15α-dihydroxy-17-methyl-20-isopropylideneprost-13-ynoic acid
116. 5,6-Epoxy-6,9α-methylene-11α-(2-tetrahydropyranyloxy)-15α-(2-tetrahydrofuranyloxy)-17-methyl-20-isopropylideneprost-13(E)-enoic acid
117. 5,6-Epoxy-6,9α-methylene-11α-acetoxy-15α-benzoyloxy-17-methyl-20-isopropylideneprostanoic acid
118. 5,6-Epoxy-6,9α-methylene-11α-hydroxy-15α-acetoxy-17-methyl-20-isopropylideneprostanoic acid
119. 5,6-Epoxy-6,9α-methylene-11α-hydroxy-15α-acetoxy-17-methyl-20-isopropylideneprost-13(E)-enoic acid
120. 5,6-Epoxy-6,9α-methylene-11α,15α-dihydroxy-16-methylprost-18-ynoic acid
121. 5,6-Epoxy-6,9α-methylene-11α,15α-dihydroxy-16-methylprost-13(E)-en-18-ynoic acid
122. 5,6-Epoxy-6,9α-methylene-11α,15α-dihydroxy-16-methylprost-13,18-diynoic acid
123. 5,6-Epoxy-6,9α-methylene-11α-hydroxy-15α-(2-tetrahydropyranyloxy)-16-methylprost-13(E)-en-18-ynoic acid
124. 5,6-Epoxy-6,9α-methylene-11α,15α-dihydroxy-16-methylprost-17-ynoic acid
125. 5,6-Epoxy-6,9α-methylene-11α,15α-dihydroxy-16-methylprost-13(E)-en-17-ynoic acid
126. 5,6-Epoxy-6,9α-methylene-11α-acetoxy-15α-hydroxy-16-methylprost-17-ynoic acid
127. 5,6-Epoxy-6,9α-methylene-11α-benzoyloxy-15α-hydroxy-16-methylprost-13(E)-en-17-ynoic acid
128. 5,6-Epoxy-6,9α-methylene-11α-hydroxy-15α-(2-tetrahydropyranyloxy)-15-cyclopentyl-16,17,18,19,20-pentanorprostanoic acid
129. 5,6-Epoxy-6,9α-methylene-11α-hydroxy-15α-(2-tetrahydropyranyloxy)-15-cyclopentyl-16,17,18,19,20-pentanorprost-13(E)-enoic acid
130. 5,6-Epoxy-6,9α-methylene-11α-(2-tetrahydropyranyloxy)-15α-hydroxy-15-cyclopentyl-16,17,18,19,20-pentanorprostanoic acid
131. 5,6-Epoxy-6,9α-methylene-11α-(2-tetrahydropyranyloxy)-15α-hydroxy-15-cyclopentyl-16,17,18,19,20-pentanorprost-13(E)-enoic acid
132. 5,6-Epoxy-6,9α-methylene-11α,15α-dihydroxy-15-cyclopentyl-16,17,18,19,20-pentanorprostanoic acid
133. 5,6-Epoxy-6,9α-methylene-11α,15α-dihydroxy-15-cyclopentyl-16,17,18,19,20-pentanorprost-13(E)-enoic acid
134. 5,6-Epoxy-6,9α-methylene-11α,15α-dihydroxy-15-cyclopentyl-16,17,18,19,20-pentanorprost-13-ynoic acid
135. 5,6-Epoxy-6,9α-methylene-11α-(2-tetrahydropyranyloxy)-15α-hydroxy-15-cyclopentyl-16,17,18,19,20-pentanorprost-13(E)-enoic acid
136. 5,6-Epoxy-6,9α-methylene-11α-hydroxy-15α-(2-tetrahydrofuranyloxy)-15-cyclopentyl-16,17,18,19,20-pentanorprost-13(E)-enoic acid
137. 5,6-Epoxy-6,9α-methylene-11α,15α-dihydroxy-15-(3-methylcyclopentyl)-16,17,18,19,20-pentanorprostanoic acid
138. 5,6-Epoxy-6,9α-methylene-11α,15α-dihydroxy-15-(3-methylcyclopentyl)-16,17,18,19,20-pentanorprost-13(E)-enoic acid
139. 5,6-Epoxy-6,9α-methylene-11α,15α-dihydroxy-15-cyclohexyl-16,17,18,19,20-pentanorprostanoic acid
140. 5,6-Epoxy-6,9α-methylene-11α,15α-dihydroxy-15-(3-ethylcyclohexyl)-16,17,18,19,20-pentanorprost-13(E)-enoic acid
141. 5,6-Epoxy-6,9α-methylene-11α,15α-dihydroxy-16,16-ethyleneprost-13(E)-enoic acid
142. 5,6-Epoxy-6,9α-methylene-11α,15α-dihydroxy-16-cyclopentyl-17,18,19,20-tetranorprost-13(E)-enoic acid
143. 5,6-Epoxy-6,9α-methylene-11α,15α-dihydroxy-16-(3-methylcyclopentyl)-17,18,19,20-tetranorprostanoic acid
144. 5,6-Epoxy-6,9α-methylene-11α,15α-dihyroxy-16-cyclohexyl-17,18,19,20-tetranorprost-13(E)-enoic acid
145. 5,6-Epoxy-6,9α-methylene-11α,15α-dihydroxy-16-cyclohexyl-17,18,19,20-tetranorprostanoic acid
146. 5,6-Epoxy-6,9α-methylene-11α,15α-dihydroxy-16,16-dimethyl-18-cyclohexyl-19,20-dinorprost-13(E)-enoic acid
147. 5,6-Epoxy-6,9α-methylene-11α,15α-dihydroxy-16-phenyl-17,18,19,20-tetranorprostanoic acid
148. 5,6-Epoxy-6,9α-methylene-11α,15α-dihydroxy-16-phenyl-17,18,19,20-tetranorprost-13(E)-enoic acid
149. 5,6-Epoxy-6,9α-methylene-11α-hydroxy-15α-(2-tetrahydropyranyloxy)-16-p-tolyl-17,18,19,20-tetranorprost-13(E)-enoic acid
150. 5,6-Epoxy-6,9α-methylene-11α,15α-dihydroxy-16-p-tolyl-17,18,19,20-tetranorprost-13(E)-enoic acid
151. 5,6-Epoxy-6,9α-methylene-11α,15α-dihydroxy-17-(p-chlorophenyl)-18,19,20-trinorprostanoic acid
152. 5,6-Epoxy-6,9α-methylene-11α,15α-dihydroxy-16-cyclopentylamino-17,18,19,20-tetranorprost-13(E)-enoic acid
153. 5,6-Epoxy-6,9α-methylene-11α,15α-dihydroxy-16-phenoxy-17,18,19,20-tetranorprostanoic acid 154. 5,6-Epoxy-6,9α-methylene-11α,15α-dihydroxy-16-phenoxy-17,18,19,20-tetranorprost-13(E)-enoic acid
155. 5,6-Epoxy-6,9α-methylene-11α,15α-dihydroxy-16-p-tolyloxy-17,18,19,20-tetranorprost-13(E)-enoic acid
156. 5,6-Epoxy-6,9α-methylene-11α,15α-dihydroxy-16-(p-chlorophenoxy)-17,18,19,20-tetranorprost-13(E)-enoic acid
157. 5,6-Epoxy-6,9α-methylene-11α,15α-dihydroxy-16-phenylthio-17,18,19,20-tetranorprostanoic acid
158. 5,6-Epoxy-6,9α-methylene-11α,15α-dihydroxy-16-phenylthio-17,18,19,20-tetranorprost-13(E)-enoic acid
159. 5,6-Epoxy-6,9α-methylene-11α,15α-dihydroxy-16-(p-bromophenylthio)-17,18,19,20-tetranorprostanoic acid
160. 5,6-Epoxy-6,9α-methylene-11α,15α-dihydroxy-16-phenylamino-17,18,19,20-tetranorprost-13(E)-enoic acid
161. 5,6-Epoxy-6,9α-methylene-11α,15α-bis(2-tetrahydropyranyloxy)-16-methylprost-13(E)-en-18-ynoic acid
162. 5,6-Epoxy-6,9α-methylene-11α,15β-dihydroxyprost-13(E)-enoic acid
163. 5,6-Epoxy-6,9α-methylene-11α,15β-dihydroxyprost-13-ynoic acid
164. 5,6-Epoxy-6,9α-methylene-11α,15β-dihydroxy-17β-methyl-20-isopropylideneprost-13(E)-enoic acid
165. 5,6-Epoxy-6,9α-methylene-11α,15β-dihydroxy-16-methylprost-13(E)-en-18-ynoic acid
166. 5,6-Epoxy-6,9α-methylene-11α,15β-dihydroxy-15-cyclopentyl-16,17,18,19,20-pentanorprost-13(E)-enoic acid The compounds listed above are the free acids, i.e. compounds of formula (I). In addition, we prefer the methyl, ethyl and benzyl esters and the sodium and potassium salts of the compounds listed above. Of the compounds listed above, particularly preferred compounds are Compounds No. 3, 4, 6, 23, 40, 41, 52, 53, 95, 96, 107, 112, 114, 116, 121, 123, 133, 135 and 161 of which Compounds No. 3, 4, 40, 52 and 161 are most preferred.

The compounds of formula (I) and salts and esters thereof may be prepared by what is effectively a 2-step process, in the first step of which the compound of formula (II):

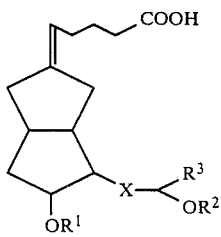

(in which $R^1$, $R^2$, $R^3$ and X are as defined above) is converted to a lactone of formula (III):

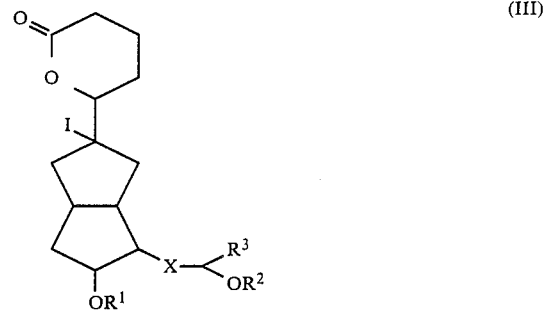

(in which $R^1$, $R^2$, $R^3$ and X are as defined above) and in the second step of which this lactone is converted to the desired compound of formula (I) or, depending upon reaction conditions and reagents, to a salt or ester thereof. If desired, these steps may be followed by salification or esterification.

In the first step, the 5Z-carbacyclin compound of formula (II) is reacted with iodine and an alkali metal iodide in the presence of a base and preferably in a solvent.

The starting material, the compound of formula (II), may be prepared, for example, by the processes described in British patent specification No. 2,012,265. British patent specification No. 2,017,699, Japanese patent application Kokai (i.e. as laid open to public inspection) No. 55/28945 or European patent application No. 11591.

The molar ratio of iodine to compound of formula (II) is preferably from 1:1 to 2:1.

Where a solvent is employed, its nature is not critical, provided that it does not adversely affect the reaction. Suitable solvents include: water; alcohols such as methanol, ethanol, propanol, isopropanol, butanol, benzyl alcohol or p-nitrobenzyl alcohol; ethers such as diethyl ether, tetrahydrofuran, dioxane, ethylene glycol dimethyl ether or diglyme; amides such as dimethylformamide or dimethylacetamide; sulphoxides such as dimethyl sulphoxide; and mixtures of any two or more thereof. Of these, alcohols are preferred.

Examples of suitable bases include: alkali metal hydroxides such as lithium hydroxide, sodium hydroxide or potassium hydroxide; alkaline earth metal hydroxides such as calcium hydroxide or barium hydroxide; alkali metal carbonates such as sodium carbonate or potassium carbonate; alkali metal bicarbonates such as sodium bicarbonate or potassium bicarbonate; and alkali metal alkoxides such as sodium methoxide, sodium ethoxide, potassium ethoxide or potassium t-butoxide. Of these, we prefer to use alkali metal carbonates or alkali metal bicarbonates. The molar ratio of base to compound of formula (II) is preferably from 1:1 to 4:1.

Examples of suitable alkali metal iodides include lithium iodide, sodium iodide and potassium iodide, of which potassium iodide is preferred. A large excess of the iodide is preferably employed, for example a molar ratio of iodide to compound of formula (II) of from 1:1 to 10:1.

The reaction temperature is not critical and, accordingly, for convenience the reaction is preferably carried out at ambient temperature. At such a temperature, the time required for the reaction will, depending upon the reactants and other reaction conditions, generally be within the range from 2 hours to 15 hours.

The second step of this reaction sequence comprises reacting the lactone of formula (III) with water or an alcohol, preferably with a compound of formula (IV):

$$R^4OH \qquad (IV)$$

(in which $R^4$ is as defined above) in the presence of a base and optionally of a solvent. Examples of suitable bases include those described in relation to the first step; where $R^4$ represents a hydrogen atom, the base is most preferably an alkali metal hydroxide or an alkali metal carbonate; when $R^4$ represents an alkyl group or an aralkyl group, the base is most preferably an alkali metal carbonate or an alkali metal alkoxide.

We prefer to employ a molar ratio of said base to said compound of formula (III) of from 1:1 to 2:1 and a molar ratio of said compound of formula (IV) or other alcohol to said compound of formula (III) of from 1:1 to 2:1.

Examples of suitable solvents include those already given for the first step. However, in this step, the compound of formula (IV) or other alcohol may serve as or as part of the solvent. Specifically, where $R^4$ represents a hydrogen atom, the compound of formula (IV) is water and, accordingly, the solvent employed for this step may be water or a mixture of water with the solvent employed for the first step. Where $R^4$ represents an alkyl or aralkyl group, the compound of formula (IV) is an alcohol and, accordingly, if an excess of this alcohol is employed, then the alcohol itself may serve as the solvent.

The temperature at which the reaction of the second step is carried out is not particularly critical and, accordingly, for convenience we prefer to carry out the reaction at about ambient temperature. At such a temperature, depending upon the reagents and other reaction conditions, the time required for the reaction will generally be within the range from 1 hour to 5 hours.

Where a compound of formula (I) itself has been prepared by the above sequence of reactions, this may, if desired, be converted to the corresponding compound in which $R^4$ represents an alkyl group or an aralkyl group by conventional esterification methods, for example by reacting the compound of formula (I) with a diazoalkane, or by converting said compound of formula (I) to its corresponding acid halide and then treating this acid halide with an alcohol of formula $R^4OH$. Correspondingly, where an alkyl or aralkyl ester of a compound of formula (I) has been prepared, this may be converted to the corresponding compound where $R^1$ represents a hydrogen atom by conventional deesterification techniques, although this is, in general, less preferred.

Similarly, the compounds may be salified, if necessary, to prepare any desired salt.

After completion of the reaction, the desired product may be recovered from the reaction mixture by conventional means. For example, one suitable recovery technique comprises: pouring the reaction mixture into water; if necessary, treating the resulting mixture with a reducing agent or acidifying it with dilute hydrochloric acid; extracting the mixture with a water-immiscible organic solvent; drying the organic extract; and finally distilling the solvent from the extract to give the desired product. This product may, if necessary, be further purified by such conventional techniques as recrystallisation, preparative thin layer chromatography or column chromatography.

If desired, the intermediate lactone compound of formula (III) obtained in the course of the above reaction sequence may be isolated and purified from the reaction mixture obtained in the first step; however, in general, it is more convenient to carry out the two steps of the above reaction sequence without intermediate isolation of the compound of formula (III).

Compounds of formula (I) can be converted to 5E-carbacyclin derivatives having potent pharmaceutical activity. This step is preferably carried out as a third step in the reaction sequence which starts with the preparation of the lactone (III) from the 5Z-carbacyclin compound (II); the step is, accordingly, referred to herein as "the third step". In this third step, the compound of formula (I) or salt or ester thereof is reacted with a compound of formula (VI):

(in which $R^5$, $R^6$ and M are as defined above), followed by reaction with a compound of formula (VII):

$$R^7—Q \qquad (VII)$$

(in which $R^7$ represents an alkyl group having from 1 to 4 carbon atoms or an aralkyl group and Q represents a halogen atom, an alkanesulphonyloxy group or an arylsulphonyloxy group).

The compound of formula (VI) is preferably prepared in situ by reaction of a compound of formula (VIII):

(in which $R^5$ and $R^6$ are as defined above and Z represents a halogen atom) with an alkali metal under a nitrogen atmosphere and in the presence of an inert solvent.

In the compound of formula (VIII), and consequently in the compound of formula (VI), $R^5$ and $R^6$, which may be the same or different, each represents a $C_1$–$C_6$ alkyl group, an aralkyl group or an aryl group. Examples of the alkyl groups, which may be straight or branched chain groups, include the methyl, ethyl, propyl, butyl and hexyl groups. Suitable aralkyl groups include the benzyl and phenethyl groups, whilst examples of suitable aryl groups include the phenyl, pentafluorophenyl, p-tolyl, p-methoxyphenyl, p-chlorophenyl and naphthyl groups. The halogen atom represented by Z in the compound of formula (VIII) is preferably a chlorine or bromine atom.

Preferred compounds of formula (VIII) include chlorodiphenylphosphine, chlorodi-p-tolylphosphine and bromodiphenylphosphine.

The preferred alkali metal for reaction with the compound of formula (VIII) and consequently for the alkali metal represented by M in the compound of formula (VI) is lithium. The molar ratio of alkali metal to compound (VIII) is preferably from 1:1 to 4:1.

The reaction of the compound of formula (VIII) with the alkali metal takes place in an inert solvent. The nature of the solvent is not critical, provided that it does not interfere with the reactor. Examples of suitable solvents include: hydrocarbons such as hexane, heptane, benzene or toluene; and ethers such as diethyl ether, tetrahydrofuran, ethylene glycol dimethyl ether and diglyme; of these, the ethers are preferred.

The second stage of this third step reaction is the reaction of the resulting compound of formula (VI) with the compound of formula (I) or salt or ester thereof. This is preferably effected in the same inert solvent as was used for the first stage of the reaction [i.e. the reaction of an alkali metal with the compound of formula (VIII)]. The third stage of the third step reaction comprises reacting the product of the second stage with a compound of formula (VII). Preferred compounds of formula (VII) are those in which $R^7$ represents a methyl group, an ethyl group or a benzyl group and Q represents a bromine atom, an iodine atom, a methanesulphonyloxy group, a benzenesulphonyloxy group or a p-toluenesulphonyloxy group. Like the second stage, the third stage of the third step reaction is preferably carried out in the same inert solvent, and preferably in the same reaction system, as was used for the first stage.

The compound of formula (VI) [and, hence, the compound of formula (VIII)] is preferably employed in a large excess relative to the compound of formula (I), for example a molar ratio of compound (VI) [or (VIII)] to compound (I) of from 1:1 to 20:1. Similarly, a large excess of said compound of formula (VII) is preferred, e.g. a molar ratio of compound (VII) to compound (I) of from 1:1 to 20:1.

Each of the three stages of the third step reaction is preferably effected at a temperature within the range from −20° C. to +100° C., more preferably at about ambient temperature. The time required for the reactions will vary, depending upon the reaction temperature, the solvent and the reagents. However, in general, the time required for the first stage is from 1 hour to 5 hours and the time required for each of the second and third stages is generally from 10 minutes to 3 hours.

After completion of the last of these reactions, the desired product of formula (V):

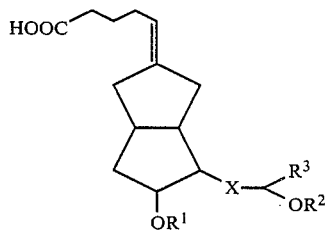
(V)

(in which $R^1$, $R^2$, $R^3$, and X are as defined above) or its salts or ester, preferably a compound of formula (Va) or (Vb), may be recovered from the reaction mixture by conventional means. For example, one suitable recovery technique comprises; pouring the reaction mixture into water; acidifying the resulting solution; extracting the solution with a water-immiscible organic solvent; drying the organic extract; and distilling the solvent from the extract to give the desired product. This product may, if necessary, be further purified by various conventional techniques, including recrystallisation, preparative thin layer chromatography or column chromatography.

Compounds of formula (I) can also be converted to a compound of formula (IX):

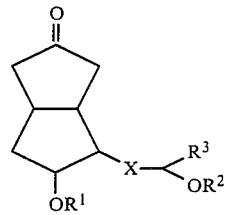
(IX)

preferably a compound of formula (IXa):

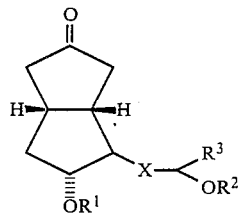
(IXa)

(in which $R^1$, $R^2$, $R^3$ and X are as defined above). This may be effected by the reactions outlined in the following reaction scheme:

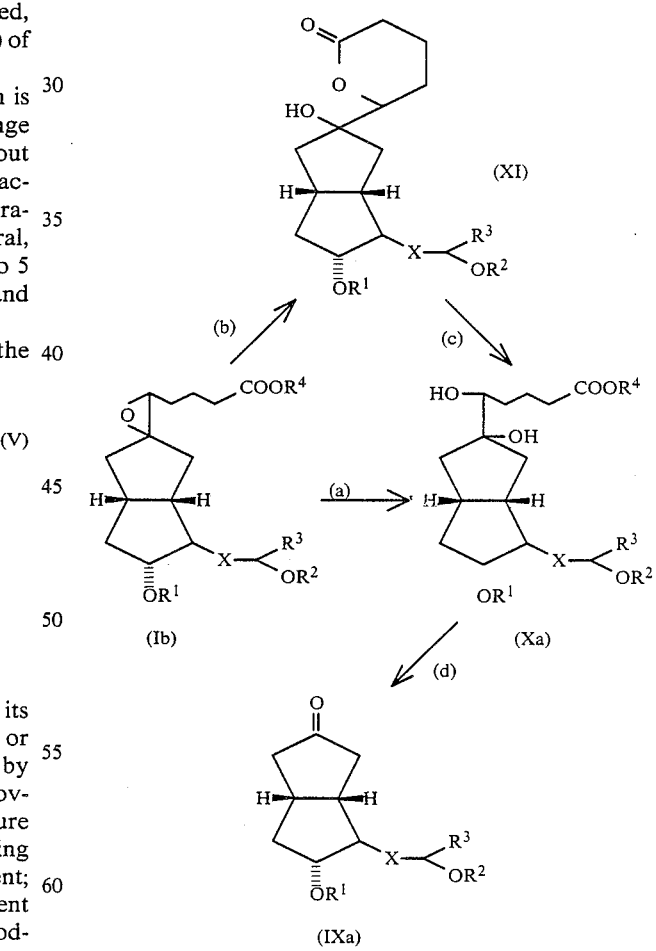

In the above formulae, $R^1$, $R^2$, $R^3$, $R^4$ and X are as defined above. The process comprising the sequence of reactions outlined in the above reaction scheme also forms part of the present invention. The reaction scheme shows the use of the preferred compounds of the invention and the preparation and use of the preferred isomers of the respective compounds. It will, of course, be appreciated that other compounds of the invention may be used and that other isomers may be prepared and used.

In step (a) of the above reaction scheme, the compound of formula (Ib) is treated with an acid or a base in an inert solvent to produce the dihydroxy compound of formula (Xa).

There is no particular limitation upon the nature of the acid used in this reaction and examples of suitable acids include, for example: mineral acids, such as hydrochloric acid, sulphuric acid, nitric acid and perchloric acid; sulphonic acids, such as methanesulphonic acid, ethanesulphonic acid, benzenesulphonic acid, p-toluenesulphonic acid or camphorsulphonic acid; and carboxylic acids, such as acetic acid or trifluoroacetic acid. Of these, acetic acid or camphorsulphonic acid are preferred. There is equally no particular limitation on the nature of the base used in this reaction, provided that it does not affect other parts of the molecule. Suitable bases include alkali metal hydroxides such as lithium hydroxide.

The nature of the solvent employed in the reaction is not critical, provided that it does not interfere with the reaction. The solvent is preferably water or a mixture of water with one or more organic solvents, which may be an alcohol (e.g. methanol or ethanol), an ether (e.g. tetrahydrofuran) or a ketone (e.g. acetone).

The reaction may be effected over a wide range of temperatures, although we generally prefer to carry out the reaction at a temperature between ambient temperature and 100° C. The time required for the reaction will vary, depending upon the reaction temperature and the reagents, but is generally within the range from 30 minutes to 10 hours.

Alternatively, where $R^4$ in the compound of formula (Ib) represents a hydrogen atom, reaction with an acid in an inert solvent may proceed via step (b) to give the hydroxy lactone of formula (XI). The acid employed in step (b) may be any one of the acids exemplified for use in step (a), as may the solvent and other reaction conditions. Depending upon the precise reaction conditions and the reagents, the reaction may proceed to give either the compound of formula (Xa) in step (a) or the compound of formula (XI) in step (b). Where the compound of formula (XI) is prepared, this may be converted to the compound of formula (Xa) by treatment with a base in an inert solvent, the bases, solvents and reaction conditions being as described for the second step of the processes of the invention, that is to say the conversion of the iodo lactone of formula (III) to the compound of formula (I).

Finally, in step (d) the compound of formula (Xa) is oxidized to give the compound of formula (IXa). The reaction involved is a simple cleavage of the carbon-carbon bond of a 1,2-diol and any oxidizing agent which can be used for this reaction in known compounds may be used in the present invention, provided that it does not affect or substantially affect the remainder of the molecule. Suitable oxidizing agents include sodium periodate and lead tetraacetate.

The oxidation reaction is preferably effected in the presence of a solvent, the nature of which is not critical, provided that it does not interfere with the reaction. Where the oxidizing agent is sodium periodate or a similar compound, preferred solvents include: water; ethers, such as tetrahydrofuran; alcohols, such as methanol or ethanol; ketones, such as acetone; fatty acids, such as acetic acid; and mixtures of two or more thereof. When lead tetraacetate or a similar compound is used as the oxidizing agent, preferred solvents are aromatic hydrocarbons, such as benzene, toluene or xylene.

The reaction temperature is not particularly critical and accordingly we normally find it convenient to carry out the reaction at about ambient temperature. Depending upon the reaction temperature and the reagents, the time required for the reaction will generally be within the range from 10 minutes to 2 hours.

After completion of each of these reaction steps, the desired product can be recovered from the reaction mixture by conventional means. For example, one suitable recovery procedure comprises: pouring the reaction mixture into water; if necessary, treating it with a reducing agent or acidifying it; extracting the mixture with a water-immiscible organic solvent; drying the organic solvent; and distilling off the solvent to give the desired product. This may, if desired, be further purified by such conventional techniques as recrystallisation, preparative thin layer chromatography and column chromatography. If desired, the individual products from each of the above steps, may be isolated and, if necessary, purified prior to treatment in the next step in the reaction sequence. Alternatively, the reaction products may be employed without intermediate isolation or without purification in the next such step.

It is of interest to note that the first, second and third steps of the processes of the invention can be employed to convert a 5E-carbacyclin compound to the corresponding 5Z-isomer and, indeed, that the reactions have more general applicability, in that they can be used to convert the E or Z isomer of any δ,ε-unsaturated carboxylic acid (or derivative thereof) to the corresponding Z or E isomer.

The invention is further illustrated by the following Examples and Preparations.

EXAMPLE 1

(a)

5-Hydroxy-6-iodo-6,9α-methylene-11α,15α-bis(2-tetrahydropyranyloxy)-17β-methyl-20-isopropylidene-prost-13(E)-enoic acid 1,5-lactone 29 ml of a 0.5N aqueous solution of sodium bicarbonate were added to a solution of 4.0 g of 6,9α-methylene-11α,15α-bis(2-tetrahydropyranyloxy)-17β-methyl-20-isopropylideneprost-5(Z),13(E)-dienoic acid in 32 ml of isopropanol. The mixture was stirred for 10 minutes, and then a solution of 3.54 g of iodine and 6.96 g of potassium iodide in 20 ml of water was added. The mixture was stirred for 6.5 hours at room temperature and then diluted with a 5% w/v aqueous solution of sodium thiosulphate. The mixture was then extracted with ethyl acetate. The extract was washed with water and dried over anhydrous sodium sulphate. The solvent was distilled off under reduced pressure, giving 4.91 g of the title compound as an oil.

Infrared Absorption Spectrum (liquid film)$\nu_{max}$ cm$^{-1}$: 1730.

Nuclear Magnetic Resonance Spectrum (CDCl$_3$)δppm: 4.64 (2H, multiplet); 5.05 (1H, triplet); 5.50 (2H, multiplet).

(b) 5,6-Epoxy-6,9α-methylene-11α,15α-bis(2-tetrahydropyranyloxy)-17β-methyl-20-isopropylideneprost-13(E)-enoic acid 10 ml of a 10% w/v aqueous solution of sodium hydroxide were added to a solution of 4.9 g of 5-hydroxy-6-iodo-6,9α-methylene-11α,15α-bis(2-tetrahydropyranyloxy)-17β-methyl-20-isopropylideneprost-13(E)-enoic acid 1,5-lactone [prepared as described in step (a) above] in 30 ml of methanol, and the mixture was stirred for 3 hours at room temperature. The mixture was then diluted with ice-water and acidified with dilute hydrochloric acid, after which it was extracted with ethyl acetate. The extract was washed with water and dried over anhydrous sodium sulphate. The solvent was then distilled off under reduced pressure, giving 4.5 g of an oily residue. This residue was purified by column chromatography through 50 g of silica gel eluted with 200 ml each of a 20%, 30%, 40%, 50% and 60% v/v mixture of ethyl acetate in hexane. 2.6 g of the title compound were obtained with the fractions eluted with 40–60% ethyl acetate in hexane.

Infrared Absorption Spectrum (liquid film)$\nu_{max}$ cm$^{-1}$: 975, 1710, 1735, 3150.

Nuclear Magnetic Resonance Spectrum (CDCl$_3$)δppm: 4.65 (2H, multiplet); 5.04 (1H, triplet); 5.5 (2H, multiplet); 9.0 (1H, multiplet).

EXAMPLE 2

Methyl 5,6-epoxy-6,9α-methylene-11α,15α-bis(2-tetrahydropyranyloxy)-17β-methyl-20-isopropylideneprost-13(E)-enoate 0.50 g of anhydrous potassium carbonate was added to a solution of 2.30 g of 5-hydroxy-6-iodo-6,9α-methylene-11α,15α-bis(2-tetrahydropyranyloxy)-17β-methyl-20-isopropylideneprost-13(E)-enoic acid 1,5-lactone [prepared as described in Example 1(a)] in 23 ml of methanol, and the mixture was stirred for 30 minutes at 60° C. The mixture was then diluted with ice-water and extracted with ethyl acetate. The extract was washed with water and dried over anhydrous sodium sulphate, after which the solvent was distilled off under reduced pressure to give 2.04 g of an oily residue. This residue was purified by column chromatography through 30 g of silica gel eluted with 200 ml each of a 5%, 10%, 20%, 30% and 40% v/v mixture of ethyl acetate in hexane. 1.36 g of the title compound was obtained from those fractions eluted with 10% and 20% ethyl acetate in hexane.

Infrared Absorption Spectrum (liquid film)$\nu_{max}$ cm$^{-1}$: 1020, 1030, 1740.

Nuclear Magnetic Resonance Spectrum (CDCl$_3$)δppm: 0.9 (3H, multiplet); 3.75 (3H, singlet); 4.75 (2H, multiplet); 4.9–5.9 (3H, multiplet).

A portion of this methyl ester was dissolved in a 80:20 by volume mixture of methanol and water and hydrolyzed with lithium hydroxide. The mixture was then evaporated to dryness, giving the lithium salt of the corresponding carboxylic acid in quantitative yield.

EXAMPLE 3

Methyl 5,6-epoxy-6,9α-methylene-11α,15α-diacetoxy-17β-methyl-20-isopropylideneprost-13(E)-enoate The procedures described in Examples 1(a) and 2 were repeated, to give 0.88 g of the title compound from 1.46 g of 6,9α-methylene-11α,15α-diacetoxy-17β-methyl-20-isopropylideneprost-5(Z),13(E)-dienoic acid.

Infrared Absorption Spectrum (liquid film)$\nu_{max}$ cm$^{-1}$: 1240, 1735.

Nuclear Magnetic Resonance Spectrum (CDCl$_3$)δppm: 0.88 (3H, doublet); 2.03 (6H, multiplet); 3.65 (3H, singlet).

EXAMPLE 4

5,6-Epoxy-6,9α-methylene-11α,15α-dihydroxy-17β-methyl-20-isopropylideneprost-13(E)-enoic acid The procedure described in Example 1(a) was repeated, to give 0.45 g of the corresponding iodo-lactone derivative from 0.40 g of 6,9α-methylene-11α,15α-dihydroxy-17β-methyl-20-isopropylideneprost-5(Z),13(E)-dienoic acid. This was then treated by the procedure described in Example 1(b), to give 0.35 g of the title compound.

Infrared Absorption Spectrum (liquid film)$\nu_{max}$ cm$^{-1}$: 1740, 3400.

EXAMPLE 5

5,6-Epoxy-6,9α-methylene-11α,15α-bis(2-tetrahydropyranyloxy)prost-13(E)-enoic acid The procedure described in Example 1(a) was repeated, to give 3.0 g of the corresponding iodo-lactone derivative from 2.5 g of 6,9α-methylene-11α,15α-bis(2-tetrahydropyranyloxy)prost-5(Z),13(E)-dienoic acid. Because the iodo-lactone derivative was unstable, the procedure described in Example 1(b) was immediately carried out, to give 1.7 g of the title compound.

Infrared Absorption Spectrum (liquid film)$\nu_{max}$ cm$^{-1}$: 975, 1710, 1735, 3150.

EXAMPLE 6

5,6-Epoxy-6,9α-methylene-11α,15α-bis(2-tetrahydropyranyloxy)-20-methoxyprost-13(E)-enoic acid The procedures of Example 1(a) and (b) were repeated, to give 0.21 g of the title compound from 0.45 g of 6,9α-methylene-11α,15α-bis(2-tetrahydropyranyloxy)-20-methoxyprost-5(Z),13(E)-dienoic acid.

Infrared Absorption Spectrum (liquid film)$\nu_{max}$ cm$^{-1}$: 970, 1710, 1735, 3150.

EXAMPLE 7

5,6-Epoxy-6,9α-methylene-11α,15α-bis(2-tetrahydropyranyloxy)-16-methylprost-13(E)-en-18-ynoic acid The procedures of Example 1(a) and (b) were repeated, to give 0.17 g of the title compound from 0.31 g of 6,9α-methylene-11α,15α-bis(2-tetrahydropyranyloxy)-16-methylprost-5(Z),13(E)-dien-18-ynoic acid.

Infrared Absorption Spectrum (liquid film)$\nu_{max}$ cm$^{-1}$: 975, 1710, 1735, 3150.

EXAMPLE 8

5,6-Epoxy-6,9α-methylene-11α,15α-bis(2-tetrahydropyranyloxy)-15-cyclopentyl-16,17,18,19,20-pentanorprost-13(E)-enoic acid The procedures described in Example 1(a) and (b) were repeated, to give 0.34 g of the title compound from 0.54 g of 6,9α-methylene-11α,15α-bis(2-tetrahydropyranyloxy)-15-cyclopentyl-16,17,18,19,20-pentanorprost-5(Z),13(E)-dienoic acid.

Infrared Absorption Spectrum (liquid film)$\nu_{max}$ cm$^{-1}$: 974, 1710, 1740, 3140.

EXAMPLE 9

5,6-Epoxy-6,9α-methylene-11α,15α-bis(2-tetrahydropyranyloxy)-16-phenoxy-17,18,19,20-tetranorprost-13(E)-enoic acid The procedures described in Example 1(a) and (b) were repeated, to give 0.38 g of the title compound in the form of an oil from 0.71 g of 6,9α-methylene-11α,1-5α-bis(2-tetrahydropyranyloxy)-16-phenoxy-17,18,19,20-tetranorprost-5(Z),13(E)-dienoic acid.

Infrared Absorption Spectrum (liquid film)$\nu_{max}$ cm$^{-1}$: 970, 1710, 1735.

EXAMPLE 10

6,9α-Methylene-11α,15α-bis(2-tetrahydropyranyloxy)-17β-methyl-20-isopropylideneprost-5(E),13(E)-dienoic acid 5 g of chlorodiphenylphosphine were added, with stirring under a stream of nitrogen, to 25 ml of anhydrous tetrahydrofuran containing 0.5 g of metallic lithium. The mixture was stirred for 2 hours at room temperature to prepare a lithium diphenylphosphide solution. 0.6 g of 5,6-epoxy-6,9α-methylene-11α,15α-bis(2-tetrahydropyranyloxy)-17β-methyl-20-isopropylideneprost-13(E)-enoic acid [as prepared in Example 1(b)] was dissolved in 6 ml of this lithium diphenylphosphide solution and then the mixture was stirred for 30 minutes under a stream of nitrogen. 1 ml of methyl iodide was then added and the mixture was stirred for a further 30 minutes at room temperature, after which it was diluted with ice-water, acidified with dilute hydrochloric acid and then extracted with ethyl acetate. The extract was washed with water and dried over anhydrous sodium sulphate. The solvent was then distilled off under reduced pressure, giving 1.4 g of a residue. This residue was purified by column chromatography through 28 g of silica gel, eluted with 200 ml each of a 10%, 15%, 20%, 25%, 30% and 35% v/v mixture of ethyl acetate in hexane. 0.4 g of the title compound was obtained from those fractions eluted with 20–30% v/v mixtures of ethyl acetate in hexane.

$[\alpha]^{26}$ + 13.6° (c = 1.0, chloroform, sodium D line).

Infrared Absorption Spectrum (liquid film)$\nu_{max}$ cm$^{-1}$: 975, 1710, 1740, 3100.

Nuclear Magnetic Resonance Spectrum (CDCl$_3$)δppm: 0.9 (3H, multiplet); 4.7 (2H, multiplet); 5.1–5.6 (4H, multiplet).

Following the same procedure, the corresponding methyl ester was treated with a 5 molar excess of lithium diphenylphosphide and the product was treated with methanol, to give the methyl ester of the title compound.

EXAMPLE 11

6,9α-Methylene-11α,15α-bis(2-tetrahydropyranyloxy)-prost-5(E),13(E)-dienoic acid The procedure described in Example 10 was repeated, to give 0.95 g of the title compound as an oil from 1.7 g of 5,6-epoxy-6,9α-methylene-11α,15α-bis(2-tetrahydropyranyloxy)prost-13(E)-enoic acid, prepared as described in Example 5.

Infrared Absorption Spectrum (liquid film)$\nu_{max}$ cm$^{-1}$: 1020, 1130, 1710, 1740, 3100.

Nuclear Magnetic Resonance Spectrum (CDCl$_3$)δppm: 4.70 (2H, multiplet); 5.0–5.6 (3H, multiplet).

EXAMPLE 12

6,9α-Methylene-11α,15α-bis(2-tetrahydropyranyloxy)-15-cyclopentyl-16,17,18,19,20-pentanorprost-5(E),1-3(E)-dienoic acid The procedures described in Examples 1(a) and (b) and 10 were followed in turn, to give 0.8 g of the title compound as an oil from 2.0 g of 6,9α-methylene-11α,1-5α-bis(2-tetrahydropyranyloxy)-15-cyclopentyl-16,17,18,19,20-pentanorprost-5(Z),13(E)-dienoic acid.

Infrared Absorption Spectrum (liquid film)$\nu_{max}$ cm$^{-1}$: 970, 1710, 1740, 3100.

Nuclear Magnetic Resonance Spectrum (CDCl$_3$)δppm: 4.71 (2H, multiplet); 5.1–5.7 (3H, multiplet).

EXAMPLE 13

6,9α-Methylene-11α,15α-bis(2-tetrahydropyranyloxy)-prost-5(E),13(E),17(Z)-trienoic acid The procedures described in Examples 1(a) and (b) and 10 were repeated in turn, to give 0.58 g of the title compound in the form of an oil from 1.47 g of 6.9α-methylene-11α,15α-bis(2-tetrahydropyranyloxy)prost-5(Z),13(E),17(Z)-trienoic acid.

Infrared Absorption Spectrum (liquid film) $\nu_{max}$ cm$^{-1}$: 978, 1023, 1035, 1710, 1740, 3100.

Nuclear Magnetic Resonance Spectrum (CDCl$_3$) δ ppm: 4.65 (2H, multiplet); 5.0–5.7 (5H, multiplet).

EXAMPLE 14

6,9α-Methylene-11α,15α-bis(2-tetrahydropyranyloxy)-20-methyleneprost-5(E),13(E)-dienoic acid The procedures described in Examples 1(a) and (b) and 10 were repeated in turn, to give 0.79 g of the title compound as an oil from 2.01 g of 6,9α-methylene-11α,15α-bis(2-tetrahydropyranyloxy)-20-methyleneprost-5(Z),13(E)-dienoic acid.

Infrared Absorption Spectrum (liquid film) $\nu_{max}$ cm$^{-1}$: 970, 1020, 1710, 3100.

Nuclear Magnetic Resonance Spectrum (CDCl$_3$) δ ppm: 4.5–6.1 (8H, multiplet).

EXAMPLE 15

6,9α-Methylene-11α,15α-bis(2-tetrahydropyranyloxy)-20-methoxyprost-5(E),13(E)-dienoic acid The procedures described in Examples 1(a) and (b) and 10 were repeated in turn, to give 0.82 g of the title compound in the form of an oil from 2.07 g of 6,9α-methylene-11α,15α-bis(2-tetrahydropyranyloxy)-20-methoxyprost-5(Z),13(E)-dienoic acid.

Infrared Absorption Spectrum (liquid film) $\nu_{max}$ cm$^{-1}$: 970, 1710, 1735, 3100.

Nuclear Magnetic Resonance Spectrum (CDCl$_3$) δ ppm: 4.71 (2H, multiplet); 3.21 (3H, singlet); 5.1–5.6 (3H, multiplet).

EXAMPLE 16

6,9α-Methylene-11α,15α-bis(2-tetrahydropyranyloxy)-16,16-dimethylprost-5(E),13(E)-dienoic acid The procedures described in Examples 1(a) and (b) and 10 were repeated in turn, to give 0.81 g of the title compound in the form of an oil from 1.97 g of 6.9α-methylene-11α,15α-bis(2-tetrahydropyranyloxy)-16,16-dimethylprost-5(Z),13(E)-dienoic acid.

Infrared Absorption Spectrum (liquid film) $\nu_{max}$ cm$^{-1}$: 970, 1710, 1735, 3100.

Nuclear Magnetic Resonance Spectrum (CDCl$_3$) δ ppm: 0.7–1.1 (9H, multiplet); 4.70 (2H, multiplet); 5.1–6.0 (3H, multiplet).

EXAMPLE 17

6,9α-Methylene-11α,15β-bis(2-tetrahydropyranyloxy)-prost-5(E),13(E)-dienoic acid The procedures described in Examples 1(a) and (b) and 10 were repeated in turn, to give 0.91 g of the title compound in the form of an oil from 2.3 g of 6.9α-methylene-11α,15β-bis(2-tetrahydropyranyloxy)-prost-5(Z),13(E)-dienoic acid.

Infrared Absorption Spectrum (liquid film) $\nu_{max}$ cm$^{-1}$: 1710, 1740, 3100.

Nuclear Magnetic Resonance Spectrum (CDCl$_3$) δ ppm: 0.7–1.1 (3H, multiplet); 4.70 (2H, multiplet); 5.0–5.6 (3H, multiplet).

EXAMPLE 18

6,9α-Methylene-11α,15α-bis(2-tetrahydropyranyloxy)-20-isopropylideneprost-5(E),13(E)-dienoic acid The procedures described in Examples 1(a) and (b) and 10 were repeated in turn, to give 0.39 g of the title compound in the form of an oil from 1.0 g of 6,9α-methylene-11α,15α-bis(2-tetrahydropyranyloxy)-20-isopropylideneprost-5(Z),13(E)-dienoic acid.

Infrared Absorption Spectrum (liquid film) $\nu_{max}$ cm$^{-1}$: 975, 1020, 1710, 1740, 3100.

Nuclear Magnetic Resonance Spectrum (CDCl$_3$) δ ppm: 4.70 (2H, multiplet); 5.1–5.9 (4H, multiplet).

EXAMPLE 19

6,9α-Methylene-11α,15α-bis(2-tetrahydropyranyloxy)-16-phenoxy-17,18,19,20-tetranorprost-5(E),13(E)-dienoic acid The procedures described in Examples 1(a) and (b) and 10 were repeated in turn, to give 0.60 g of the title compound in the form of an oil from 1.50 g of 6,9α-methylene-11α,15α-bis(2-tetrahydropyranyloxy)-16-phenoxy-17,18,19,20-tetranorprost-5(Z),13(E)-dienoic acid.

Infrared Absorption Spectrum (liquid film) $\nu_{max}$ cm$^{-1}$: 970, 1030, 3100.

Nuclear Magnetic Resonance Spectrum (CDCl$_3$) δ ppm: 6.80–7.50 (5H, multiplet).

EXAMPLE 20

6,9α-Methylene-11α,15α-bis(2-tetrahydropyranyloxy)-16,20-dimethylprost-5(E),13(E)-dienoic acid The procedures described in Examples 1(a) and (b) and 10 were repeated in turn, to give 0.85 g of the title compound in the form of an oil from 2.05 g of 6,9α-methylene-11α,15α-bis(2-tetrahydropyranyloxy)-16,20-dimethylprost-5(Z),13(E)-dienoic acid.

Infrared Absorption Spectrum (liquid film) $\nu_{max}$ cm$^{-1}$: 970, 1710, 1740, 3100.

Nuclear Magnetic Resonance Spectrum (CDCl$_3$) δ ppm: 0.7–1.1 (6H, multiplet); 4.70 (2H, multiplet); 5.0–5.7 (3H, multiplet).

EXAMPLE 21

6,9α-Methylene-11α,15α-bis(2-tetrahydropyranyloxy)-16-methylprost-5(E),13(E)-dien-18-ynoic acid The procedures described in Examples 1(a) and (b) and 10 were repeated in turn, to give 0.8 g of the title compound in the form of an oil from 1.96 g of 6,9α-methylene-11α,15α-bis(2-tetrahydropyranyloxy)-16-methylprost-5(Z),13(E)-dien-18-ynoic acid Infrared Absorption Spectrum (liquid film) $\nu_{max}$ cm$^{-1}$: 970, 1710, 1735, 2960, 3100.

Nuclear Magnetic Resonance Spectrum (CDCl$_3$) δ ppm: 0.9 (3H, multiplet); 1.75 (3H, triplet); 4.70 (2H, multiplet); 5.0–5.7 (3H, multiplet).

PREPARATION 1

Methyl 5,6,11α,15α-tetrahydroxy-6,9α-methylene-17β-methyl-20-isopropylideneprost-13(E)-enoate 11 ml of water and 0.10 g of camphorsulphonic acid were added to a solution of 0.70 g of methyl 5,6-epoxy-6,9α-methylene-11α,15α-bis(2-tetrahydropyranyloxy)-17β-methyl-20-isopropylideneprost-13(E)-enoate in 30 ml of acetone, and the mixture was stirred for 1 hour at room temperature and then for 3 hours at 40° C. The mixture was then diluted with an aqueous solution of sodium chloride and extracted with ethyl acetate. The extract was washed with water and dried over anhydrous sodium sulphate. The solvent was then distilled from the extract under reduced pressure, giving 0.72 g of an oily residue. This residue was purified by column chromatography through 15 g of silica gel eluted with 200 ml each of a 50%, 60%, 70%, 80% and 90% mixture of ethyl acetate in hexane and with 100% ethyl acetate. 0.35 g of the title compound was obtained from the fractions eluted with 70–100% ethyl acetate in hexane.

Infrared Absorption Spectrum (liquid film) $\nu_{max}$ cm$^{-1}$: 970, 1725, 3400.

Nuclear Magnetic Resonance Spectrum (CDCl$_3$) δ ppm: 0.9 (3H, doublet); 3.64 (3H, singlet); 5.05 (1H, triplet); 5.47 (2H, multiplet).

The procedure of this example described above was repeated exactly, except that the camphorsulphonic acid was replaced by acetic acid. Deprotection of the protected hydroxy groups did not occur and the product was methyl 5,6-dihydroxy-6,9α-methylene-11α,15α-bis(2-tetrahydropyranyloxy)-17β-methyl-20-isopropylideneprost-13(E)-enoate.

PREPARATION 2

5,6-Dihydroxy-6,9α-methylene-11α,15α-bis(2-tetrahydropyranyloxy)-17β-methyl-20-isopropylideneprost-13(E)-enoic acid 1,5-lactone 0.8 g of 5,6-epoxy-6,9α-methylene-11α,15α-bis(2-tetrahydropyranyloxy)-17β-methyl-20-isopropylideneprost-13(E)-enoic acid [prepared as described in Example 1(b)] was dissolved in a mixture of methanol and ethyl acetate and then treated with 5% w/v hydrochloric acid. The resulting organic layer was separated, washed and dried over anhydrous sodium sulphate. The solvent was then distilled off under reduced pressure and the residue was purified by column chromatography through silica gel, to give 0.5 g of the title compound.

Infrared Absorption Spectrum (liquid film) $\nu_{max}$ cm$^{-1}$: 1020, 1735, 3450.

PREPARATION 3

Methyl 5,6-dihydroxy-6,9α-methylene-11α,15α-bis(2-tetrahydropyranyloxy)-17β-methyl-20-isopropylideneprost-13(E)-enoate 0.22 g of 5,6-dihydroxy-6,9α-methylene-11α,15α-bis(2-tetrahydropyranyloxy)-17β-methyl-20-isopropylideneprost-13(E)-enoic acid 1,5-lactone (prepared as described in Preparation 2) was dissolved in 10 ml of methanol. To this solution were added 50 mg of anhydrous potassium carbonate, and the mixture was stirred for 1 hour at room temperature. It was then diluted with water and extracted with ethyl acetate. The extract was washed with water and dried over anhydrous sodium sulphate. The solvent was then distilled off under reduced pressure, giving 0.20 g of the title compound in the form of an oil.

Infrared Absorption Spectrum (liquid film) $\nu_{max}$ cm$^{-1}$: 1020, 1740, 3460.

Hydrolysis of this ester with an alkali afforded the corresponding carboxylic acid.

PREPARATION 4

3α-Hydroxy-2-(3α-hydroxy-5β,9-dimethyl-1,8-decadienyl)-7-oxobicyclo[3.3.0]octane 0.30 g of methyl 5,6,11α,15α-tetrahydroxy-6,9α-methylene-17β-methyl-20-isopropylideneprost-13(E)-enoate (prepared as described in Preparation 1) was dissolved in 14 ml of a 4:2:1 by volume mixture of acetone, acetic acid and water. 0.17 g of sodium periodate was added to this solution, and the mixture was stirred for 1 hour at room temperature. It was then diluted with water and salted out. The resulting mixture was extracted with ethyl acetate. The extract was washed with water and dried over anhydrous sodium sulphate. The solvent was distilled off under reduced pressure, giving 0.27 g of an oily residue, which was purified by column chromatography through 7.5 g of silica gel, to give 0.15 g of the title compound as an oil.

Infrared Absorption Spectrum (liquid film) $\nu_{max}$ cm$^{-1}$: 970, 1090, 1740, 3400.

Nuclear Magnetic Resonance Spectrum (CDCl$_3$) δ ppm: 0.9 (3H, doublet); 5.1 (1H, triplet); 5.5 (2H, multiplet).

PREPARATION 5

2-[5β,9-Dimethyl-3α-(2-tetrahydropyranyloxy)-1,8-decadienyl]-7-oxo-3α-(2-tetrahydropyranyloxy)bicyclo[3.3.0]octane 0.18 g of methyl 5,6-dihydroxy-6,9α-methylene-11α,15α-bis(2-tetrahydropyranyloxy)-17β-methyl-20-isopropylideneprost-13(E)-enoate (prepared as described in Preparation 3) were dissolved in 10 ml of benzene. Lead tetraacetate was added to the solution and the mixture was stirred for 20 minutes at room temperature, after which an acetone solution of sodium iodide was added. The mixture was then washed with an aqueous solution of sodium thiosulphate and the organic layer was separated. This organic layer was washed with water and dried over sodium sulphate, after which the solvent was distilled off under reduced pressure, to give 0.17 g of an oily residue. This residue was purified by column chromatography through 10 g of silica gel eluted with 200 ml each of a 5%, 10%, 20% and 30% mixture of ethyl acetate in hexane. 0.117 g of the title compound was obtained from the fractions eluted with 20 and 30% ethyl acetate in hexane.

Infrared Absorption Spectrum (liquid film) $\nu_{max}$ cm$^{-1}$: 970, 1020, 1030, 1130, 1742.

Nuclear Magnetic Resonance Spectrum (CDCl$_3$) δ ppm: 0.9 (3H, multiplet); 4.68 (2H, multiplet); 5.1 (1H, triplet); 5.35–5.65 (2H, multiplet).

PREPARATION 6

3α-Acetoxy-2-(3α-acetoxy-5β,9-dimethyl-1,8-decadienyl)-7-oxobicyclo[3.3.0]octane The procedures described in Preparations 1 and 4 were repeated, in turn, to give 0.30 g of the title compound from 0.88 g of methyl 5,6-epoxy-6,9α-methylene-11α,15α-diacetoxy-17β-methyl-20-isopropylideneprost-13(E)-enoate (prepared as described in Example 3).

Infrared Absorption Spectrum (liquid film) $\nu_{max}$ cm$^{-1}$: 1240, 1735.

PREPARATION 7

3α-Hydroxy-2-(3α-hydroxy-5β,9-dimethyl-1,8-decadienyl)-7-oxobicyclo[3.3.0]octane The procedures described in Preparations 1 and 4 were repeated in turn, to give 0.30 g of the title compound from 0.6 g of 5,6-epoxy-6,9α-methylene-11α,15α-dihydroxy-17β-methyl-20-isopropylideneprost-13(E)-enoic acid (prepared as described in Example 4).

Infrared Absorption Spectrum (liquid film) $\nu_{max}$ cm$^{-1}$: 1733, 3380.

PREPARATION 8

Lithium 5,6-dihydroxy-6,9α-methylene-11α,15α-bis(2-tetrahydropyranyloxy)-17β-methyl-20-isopropylideneprost-13(E)-enoate 0.63 g of methyl 5,6-epoxy-6,9α-methylene-11α,15α-bis(2-tetrahydropyranyloxy)-17β-methyl-20-isopropylideneprost-13(E)-enoate (prepared as described in Example 2) was dissolved in 10 ml of methanol. 4 ml of water and 55 mg of lithium hydroxide monohydrate were added to the solution, which was then stirred at 60° C. for 5 hours. At the end of this time, water and methanol were distilled off under reduced pressure and the residue was dissolved in benzene. From this, the water was removed by azeotropic distillation and the remaining solvent was distilled off under reduced pressure, to give 0.63 g of the title compound in the form of a glass.

Infrared Absorption Spectrum (Nujol-trade markmull) $\nu_{max}$ cm$^{-1}$: 1020, 1580, 3380.

Nuclear Magnetic Resonance Spectrum (CDCl$_3$) δ ppm: 4.7 (2H, multiplet); 5.0–5.7 (3H, multiplet).

Treatment of this lithium salt with dilute aqueous hydrochloric acid followed by conventional recovery procedures gave the corresponding free acid.

PREPARATION 9

2-[5β,9-dimethyl-3α-(2-tetrahydropyranyloxy)-1,8-decadienyl]-7-oxo-3α-(2-tetrahydropyranyloxy)bicyclo[3.3.0]octane The procedure described in Preparation 5 was repeated, to give 0.37 g of the title compound from 0.54 g of lithium 5,6-dihydroxy-6,9α-methylene-11α,15α-bis(2-tetrahydropyranyloxy)-17β-methyl-20-isopropylideneprost-13(E)-enoate (prepared as described in Preparation 8). The product had identical properties with the product of Preparation 5.

PREPARATION 10

Lithium 5,6-dihydroxy-6,9α-methylene-11α,15α-bis(2-tetrahydropyranyloxy)-15-cyclopentyl-16,17,18,19,20-pentanorprost-13(E)-enoate The procedure described in Preparation 8 was repeated except that twice the amount of base was used, to give 0.50 g of the title compound in the form of a glass from 0.51 g of 5,6-epoxy-6,9α-methylene-11α,15α-bis(2-tetrahydropyranyloxy)-15-cyclopentyl-16,17,18,19,20-pentanorprost-13(E)-enoic acid.

Infrared Absorption Spectrum (Nujol mull) $\nu_{max}$ cm$^{-1}$: 1020, 1580, 3380.

Nuclear Magnetic Resonance Spectrum (CDCl$_3$) δ ppm: 4.8 (2H, multiplet); 5.1–5.7 (2H, multiplet).

PREPARATION 11

Lithium 5,6-dihydroxy-6,9α-methylene-11α,15α-bis(2-tetrahydropyranyloxy)prost-13(E)-enoate The procedure described in Preparation 8 was repeated, to give 0.72 g of the title compound in the form of a glass from 0.75 g of 5,6-epoxy-6,9α-methylene-11α,15α-bis(2-tetrahydropyranyloxy)prost-13(E)-enoic acid (prepared as described in Example 5).

Infrared Absorption Spectrum (Nujol mull) $\nu_{max}$ cm$^{-1}$: 1020, 1580, 3380.

Nuclear Magnetic Resonance Spectrum (CDCl$_3$) δ ppm: 4.7 (2H, multiplet); 5.1–5.7 (2H, multiplet).

PREPARATION 12

By following the procedure described in Preparation 8, lithium 5,6-dihydroxy-6,9α-methylene-11α,15α-bis-(2-tetrahydropyranyloxy)-20-methoxyprost-13(E)-enoate or lithium 5,6-dihydroxy-6,9α-methylene-11α,15α-bis-(2-tetrahydropyranyloxy)-16-methylprost-13(E)-en-18-ynoate were obtained from 5,6-epoxy-6,9α-methylene-11α,15α-bis(2-tetrahydropyranyloxy)-20-methoxyprost-13(E)-enoic acid (prepared as described in Example 6) or 5,6-epoxy-6,9α-methylene-11α,15α-bis-(2-tetrahydropyranyloxy)-16-methylprost-13(E)-en-18-ynoic acid (prepared as described in Example 7), respectively. Both lithium salts had the same infrared spectra.

Infrared Absorption Spectrum (Nujol mull) $\nu_{max}$ cm$^{-1}$: 1020, 1580, 3380.

PREPARATION 13

Lithium 5,6-dihydroxy-6,9α-methylene-11α,15α-bis(2-tetrahydropyranyloxy)-16-phenoxy-17,18,19,20-tetranorprost-13(E)-enoate The procedure described in Preparation 8 was repeated, to give 0.34 g of the title compound in the form of a glass from 0.38 g of 5,6-epoxy-6,9α-methylene-11α,15α-bis(2-tetrahydropyranyloxy)-16-phenoxy-17,18,19,20-tetranorprost-13(E)-enoic acid (prepared as described in Example 9).

Infrared Absorption Spectrum (Nujol mull) $\nu_{max}$ cm$^{-1}$: 1020, 1580, 3380.

Nuclear Magnetic Resonance Spectrum (CDCl$_3$) δ ppm: 4.7 (2H, multiplet); 5.1–5.7 (2H, multiplet).

We claim:

1. Compounds of formula (I):

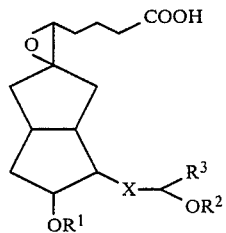

in which:

R$^1$ and R$^2$ are the same or different and each represents hydrogen or a hydroxy-protecting group;

R$^3$ represents an alkyl group having from 1 to 12 carbon atoms which is optionally substituted, an alkenyl group having from 2 to 12 carbon atoms, an alkynyl group having from 2 to 6 carbon atoms or a cycloalkyl group which is optionally substituted; and X represents an ethylene group, a trans-vinylene group or an ethynylene group and salts and esters thereof.

2. Compounds as claimed in claim 1, wherein:

R$^1$ and R$^2$ are the same or different and each represents hydrogen or a hydroxy-protecting group;

R$^3$ represents a C$_4$–C$_{10}$ alkyl group which is unsubstituted or which has one or more fluorine, methoxy or ethoxy substituents; a C$_1$–C$_3$ alkyl group having one or more cyclopentyl, 3-methylcyclopentyl, 3-ethylcyclopentyl, cyclohexyl, 3-methylcyclohexyl, 3-ethylcyclohexyl, phenyl, p-trifluoromethylphenoxy, phenoxy, phenylthio or p-tolyloxy substituents; a C$_4$–C$_{12}$ alkenyl group; a C$_4$–C$_6$ alkynyl group; cyclopentyl; 3-methylcyclopentyl; 3-ethylcyclopentyl; cyclohexyl; 3-methylcyclohexyl; or 3-ethylcyclohexyl; and X represents an ethylene, trans-vinylene or ethynylene group;

and salts and aralkyl and C$_1$–C$_4$ alkyl esters thereof.

3. Compounds as claimed in claim 2, wherein:

R$^1$ and R$^2$ are the same or different and each represents: hydrogen; a C$_1$–C$_4$ alkyl group having at its α-position a C$_1$–C$_4$ alkoxy, C$_1$–C$_4$ alkylthio, aralkyloxy or trihalomethyl substituent; a 2-methoxyethoxymethyl group; a tetrahydrofuran-2-yl group; a tetrahydro-pyran-2-yl group; a 4-methoxytetrahydrothiopyran-4-yl group; a trialkylsilyl or dialkylphenylsilyl group, in which each alkyl group has from 1 to 4 carbon atoms; acetyl; propionyl; or benzoyl;

and salts and aralkyl and C$_1$–C$_4$ alkyl esters thereof.

4. Compounds as claimed in claim 1, wherein:

R$^1$ and R$^2$ are the same or different and each represents a hydrogen atom or a methoxymethyl, tetrahydropyran-2-yl, t-butyl-dimethylsilyl, acetyl or benzoyl group;

R$^3$ represents a pentyl, 1-methylpentyl, hexyl, 1-methylhexyl, 1,1-dimethylpentyl, 2-methylhexyl, 2-ethoxy-1,1-dimethylethyl, 5-methoxypentyl, 5-methoxy-1-methylpentyl, 1-fluoropentyl, cyclopentylmethyl, 3-methylcyclopentylmethyl, 2-cyclopentylethyl, 2-cyclopentyl-1-methylethyl, cyclohexylmethyl, 3-ethylcyclohexylmethyl, 2-cyclohexylethyl, benzyl, phenethyl, p-methyl-benzyl, phenoxymethyl, m-chlorophenoxymethyl, phenylthiomethyl, 2-pentenyl, 4-pentenyl, 4-hexenyl, 5-hexenyl, 6-methyl-5-heptenyl, 2,6-dimethyl-5-heptenyl, 3-pentynyl, 1-methyl-2-pentynyl, 1-methyl-3-pentynyl, cyclopentyl, 3-ethylcyclopentyl, cyclohexyl, 3-methylcyclohexyl or 1-butylcyclopropyl group; and X represents an ethylene or trans-vinylene group; and salts and methyl or ethyl esters thereof.

5. Compounds as claimed in claim 1, wherein:
$R^1$ and $R^2$ are the same or different and each represents a hydrogen atom, a tetrahydropyran-2-yl group, a t-butyl-dimethylsilyl group or an acetyl group;
$R^3$ represents a pentyl, 1-methylhexyl, 1,1-dimethylpentyl, 5-methoxypentyl, phenoxymethyl, 2-pentenyl, 4-pentenyl, 4-hexenyl, 5-hexenyl, 6-methyl-5-heptenyl, 2,6-dimethyl-5-heptenyl, 1-methyl-3-pentynyl or cyclopentyl group; and
X represents a trans-vinylene group;
and salts and methyl esters thereof.

6. Compounds as claimed in claim 1 having the formula (Ia):

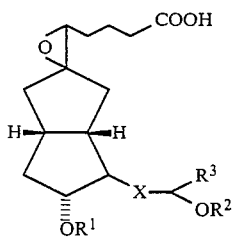

(Ia)

wherein $R^1$, $R^2$, $R^3$ and X are as defined in claim 1 and salts and esters thereof.

7. Compounds as claimed in claim 6, wherein:
$R^1$ and $R^2$ are the same or different and each represents a hydrogen atom, a tetrahydropyran-2-yl group, a t-butyl-dimethylsilyl group or an acetyl group;
$R^3$ represents a pentyl, 1-methylhexyl, 1,1-dimethylpentyl, 5-methoxypentyl, phenoxymethyl, 2-pentenyl, 4-pentenyl, 4-hexenyl, 5-hexenyl, 6-methyl-5-heptenyl, 2,6-dimethyl-5-heptenyl, 1-methyl-3-pentynyl or cyclopentyl group; and
X represents a trans-vinylene group;
and salts and methyl esters thereof.

8. Compounds as claimed in claim 1 having the formula (Ib):

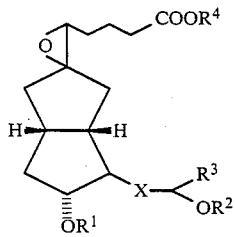

(Ib)

wherein $R^1$, $R^2$, $R^3$ and X are as defined in claim 1 and $R^4$ represents hydrogen, $C_1$-$C_4$ alkyl or aralkyl, and salts thereof.

9. Compounds as claimed in claim 8, wherein:
$R^1$ and $R^2$ are the same or different and each represents a hydrogen atom, a tetrahydropyran-2-yl group, a t-butyl-dimethylsilyl group or an acetyl group;
$R^3$ represents a pentyl, 1-methylhexyl, 1,1-dimethylpentyl, 5-methoxypentyl, phenoxymethyl, 2-pentenyl, 4-pentenyl, 4-hexenyl, 5-hexenyl, 6-methyl-5-heptenyl, 2,6-dimethyl-5-heptenyl, 1-methyl-3-pentynyl or cyclopentyl group;
X represents a trans-vinylene group; and
$R^4$ represents hydrogen or methyl;
and salts thereof.

10. Compounds as claimed in claim 1, selected from the group consisting of:
5,6-Epoxy-6,9α-methylene-11α,15α-bis(2-tetrahydropyranyloxy)prost-13(E)-enoic acid
5,6-Epoxy-6,9α-methylene-11α,15α-bis(2-tetrahydrofuranyloxy)prost-13-ynoic acid
5,6-Epoxy-6,9α-methylene-11α,15α-bis(2-tetrahydropyranyloxy)-20-methylprost-13(E)-enoic acid
5,6-Epoxy-6,9α-methylene-11α,15α-bis(2-tetrahydropyranyloxy)-17-methyl-20-isopropylideneprost-13(E)-enoic acid
5,6-Epoxy-6,9α-methylene-11α,15α-diacetoxy-17β-methyl-20-isopropylideneprost -13(E)-enoic acid
5,6-Epoxy-6,9α-methylene-11α,15α-bis(2-tetrahydropyranyloxy)-15α-cyclopentyl-16,17,18,19,20-pentanorprost-13(E)-enoic acid
5,6-Epoxy-6,9α-methylene-11α,15α-bis(t-butyl-dimethylsilyloxy)-15-cyclopentyl-16,17,18,19,20-pentanorprost-13(E)-enoic acid
5,6-Epoxy-6,9α-methylene-11α,15α-dihydroxyprost-13(E)-enoic acid
5,6-Epoxy-6,9α-methylene-11α,15α-dihydroxyprost-13-ynoic acid
5,6-Epoxy-6,9α-methylene-11α,15α-dihydroxy-16,16-dimethylprost-13(E)-enoic acid
5,6-Epoxy-6,9α-methylene-11α,15α-dihydroxy-17β-methyl-20-isopropylideneprost-13(E)-enoic acid
5,6-Epoxy-6,9α-methylene-11α-(2-tetrahydropyranyloxy)-15α-hydroxy-17-methyl-20-isopropylideneprost-13(E)-enoic acid
5,6-Epoxy-6,9α-methylene-11α-(2-tetrahydropyranyloxy)-15α-(2-tetrahydrofuranyloxy)-17-methyl-20-isopropylideneprost-13(E)-enoic acid
5,6-Epoxy-6,9α-methylene-11α,15α-dihydroxy-16-methylprost-13(E)-en-18-ynoic acid
5,6-Epoxy-6,9α-methylene-11α-hydroxy-15α-(2-tetrahydropyranyloxy)-16-methylprost-13(E)-en-18-ynoic acid
5,6-Epoxy-6,9α-methylene-11α,15α-dihydroxy-15-cyclopentyl-16,17,18,19,20-pentanorprost-13(E)-enoic acid
and
5,6-Epoxy-6,9α-methylene-11α-(2-tetrahydropyranyloxy)-15α-hydroxy-15-cyclopentyl-16,17,18,19,20-pentanorprost-13(E)-enoic acid
5,6-Epoxy-6,9α-methylene-11α,15α-bis(2-tetrahydropyranyloxy)-16-methylprost-13(E)-en-18-ynoic acid and sodium and potassium salts and methyl, ethyl and benzyl esters thereof.

* * * * *